US010982239B2

(12) United States Patent
Kuivanen et al.

(10) Patent No.: US 10,982,239 B2
(45) Date of Patent: Apr. 20, 2021

(54) METHOD FOR PRODUCING MESO-GALACTARIC ACID BY CONTACTING A FUNGAL CELL WITH A BIOMATERIAL HAVING GALACTURONIC ACID

(71) Applicant: TEKNOLOGIAN TUTKIMUSKESKUS VTT OY, Espoo (FI)

(72) Inventors: Joosu Kuivanen, Espoo (FI); Peter Richard, Espoo (FI); Ying-Mong Jasmin Wang, Espoo (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 16/302,836

(22) PCT Filed: May 19, 2017

(86) PCT No.: PCT/FI2017/050378
§ 371 (c)(1),
(2) Date: Nov. 19, 2018

(87) PCT Pub. No.: WO2017/198908
PCT Pub. Date: Nov. 23, 2017

(65) Prior Publication Data
US 2019/0256875 A1    Aug. 22, 2019

(30) Foreign Application Priority Data
May 20, 2016   (FI) .................................. 20165425

(51) Int. Cl.
| | |
|---|---|
| C12P 7/58 | (2006.01) |
| C12N 9/04 | (2006.01) |
| C12N 9/02 | (2006.01) |
| C12P 7/42 | (2006.01) |
| C12P 7/44 | (2006.01) |
| C12R 1/685 | (2006.01) |
| C12R 1/69 | (2006.01) |
| C12R 1/885 | (2006.01) |
| C12Q 1/26 | (2006.01) |

(52) U.S. Cl.
CPC .............. *C12P 7/58* (2013.01); *C12N 9/0006* (2013.01); *C12N 9/0008* (2013.01); *C12P 7/42* (2013.01); *C12P 7/44* (2013.01); *C12Q 1/26* (2013.01); *C12R 1/685* (2013.01); *C12R 1/69* (2013.01); *C12R 1/885* (2013.01); *C12Y 101/01021* (2013.01); *C12Y 101/01035* (2013.01); *C12Y 101/01203* (2013.01); *C12Y 102/01031* (2013.01); *C12Y 501/02002* (2013.01)

(58) Field of Classification Search
None
See application file for complete search history.

(56) References Cited

U.S. PATENT DOCUMENTS 8,895,273 B2 * 11/2014 Boer .................. C12P 7/44
                                                   435/142

FOREIGN PATENT DOCUMENTS

WO    WO 2010/072902    7/2010

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession EHA19692. Oct. 12, 2011 (Year: 2011).*
Wiebe et al. BMC Biotechnology 2010, 10:63 (Year: 2010).*
Barratt et al., "Wild-Type and Mutant Stocks of *Aspergillus Nidulans*" *Genetics*, vol. 52: 233-246 (Jul. 1965).
Benz et al., "Identification and characterization of a galacturonic acid transporter from *Neurospora crassa* and its application for *Saccharomyces cerevisiae* fermentation processes" *Biotechnology for Biofuels*, vol. 7: 20, pp. 1-13 (2014).
Chang et al., "Hexuronic Acid Dehydrogenase of *Agrobacterium tumefaciens*" *Journal of Bacteriology*, vol. 99, No. 3: 667-673 (Sep. 1969).
Chang et al., "D-Glucaric Acid and Galactaric Acid Catabolism by *Agrobacterium tumefaciens*" *Journal of Bacteriology* vol. 102, No. 1: 85-96 (Apr. 1970).
Dagley et al., "The Metabolism of Galactarate, D-Glucarate and Various Pentoses by Species of *Pseudomonas*" *Biochem. J.*, vol. 95: 48-58 (1965).
Kuivanen et al., "Conversion of orange peel to L-galactonic acid in a consolidated process using engineered strains of *Aspergillus niger*" *AMB Express*, vol. 4: 33, pp. 1-8 (2014).
Kuivanen et al., "Metabolic engineering of the fungal D-galacturonate pathway for L-ascorbic acid production" *Microbial Cell Factories*, vol. 14:2, pp. 2-9 (2015).
Kuivanen et al., "A novel pathway for fungal D-glucuronate catabolism contains an L-idonate forming 2-keto-L-gulonate reductase" *Scientific reports*, vol. 6: 26329, pp. 1-9 (May 18, 2016).
Kuivanen et al., "Engineering *Aspergillus niger* for galactaric acid production: elimination of galactaric acid catabolism by using RNA sequencing and CRISPR/Cas9" *Microbial Cell Factories*, vol. 15, No. 1: 1-9 (Dec. 12, 2016) XP055396989.
Liu et al., "Efficient genome editing in filamentous fungus *Trichoderma reesei* using the CRISPR/Cas9 system" *Cell Discovery*, vol. 1, No. 15007, pp. 1-11 (Jul. 15, 2015).
Martens-Uzunova et al., "An evolutionary conserved d-galacturonic acid metabolic pathway operates across filamentous fungi capable of pectin degradation" *Fungal Genetics and Biology*, vol. 45, No. 11: 1449-1457 (Nov. 2008).

(Continued)

*Primary Examiner* — Christian L Fronda
(74) *Attorney, Agent, or Firm* — Nixon & Vanderhye P.C.

(57) ABSTRACT

The present invention relates to a field of genetically modified fungal cells and converting galacturonic acid to meso-galactaric acid, more precisely to a method of producing meso-galactaric acid. The invention further relates to recombinant fungal cells having a specific combination of modifications including but not limited to expression of uronate dehydrogenase enzyme, reduced D-galacturonic acid reductase activity, and furthermore reduced meso-galactaric acid catabolism, as well as uses and methods related thereto.

12 Claims, 4 Drawing Sheets

Specification includes a Sequence Listing.

(56) References Cited

OTHER PUBLICATIONS

Martens-Uzunova et al., "Assessment of the pectin degrading enzyme network of *Aspergillus niger* by functional genomics" *Fungal Genetics and Biology*, vol. 46, Suppl. 1: S170-S179 (Mar. 2009).

Mohnen, "Pectin structure and biosynthesis" *Current Opinion in Plant Biology*, vol. 11: 266-277 (2008).

Mojzita et al., "Metabolic Engineering of Fungal Strains for Conversion of D-Galacturonate to *meso*-Galactarate" *Applied and Environmental Microbiology* vol. 76, No. 1: 169-175 (Jan. 2010).

Motter et al., "Categorisation of sugar acid dehydratases in *Aspergillus niger*" *Fungal Genetics and Biology*, vol. 64: 67-72, (Mar. 2014), XP028611138.

Napora-Wijata et al., "Biocatalytic reduction of carboxylic acids" *Biotechnol. J.*, vol. 9: 822-843 (2014).

Nødvig et al., "A CRISPR-Cas9 System for Genetic Engineering of Filamentous Fungi" *PLOS ONE*, vol. 10, No. 7: e0133085, pp. 1-18 (2015).

O'Neill et al., "Rhamnogalacturonan II: Structure and Function of a Borate Cross-Linked Cell Wall Pectic Polysaccharide" *Ann. Rev. Plant Biol.*, vol. 55: 109-139 (2004).

Pohl et al., "CRISPR/Cas9 Based Genome Editing of *Penicillium chrysogenum*" *ACS Synthetic Biology*, vol. 5: 754-764 (2016).

Rautiainen et al., "Selective oxidation of uronic acids into aldaric acids over gold catalyst" *RSC Advances*, vol. 5: 19502-19507 (2015).

Richard et al. Cloning and Expression of a Fungal L-Arabinitol 4-Dehydrogenase Gene, vol. 276, No. 44: 40631-40637 (Nov. 2, 2001).

Richard et al., "D-Galacturonic acid catabolism in microorganisms and its biotechnological relevance" *Appl. Microbiol. Biotechnol.*, vol. 82: 597-604 (2009).

*Trichoderma reesei* RUT C-30 v1.0, Dec. 4, 2013 (Dec. 4, 2013), JGI [Retrieved on Sep. 7, 2016], Retrieved from the Internet, Protein ID No. 39114, Database <URL: http://genome.jgi.doe.gov/cgi-bin/dispGeneModel?db=TrireRUTC30_1&id=39114>.

Wang, "Characterization and engineering of hexaric and hexuronic acid pathways in fungal microorganisms" Master's thesis, Aalto University, 4 pages (Jun. 14, 2016).

Zhang et al., "The D-galacturonic acid catabolic pathway in *Botrytis cinerea*" *Fungal Genetics and Biology*, vol. 48, No. 10: 990-997 (Oct. 2011).

Zhang (C) et al., "Highly efficient CRISPR mutagenesis by microhomology-mediated end joining in *Aspergillus fumigatus*" *Fungal Genetics and Biology*, vol. 86: 47-57 (2016).

Zhang (H) et al., "Production of Adipic Acid from Sugar Beet Residue by Combined Biological and Chemical Catalysis" *ChemCatChem*, vol. 8: 1500-1506 (2016).

Office Action issued in FI Appln. No. 20165425 dated Sep. 9, 2016.

International Search Report issued in PCT/FI2017/050378 dated Aug. 21, 2017.

* cited by examiner

A.
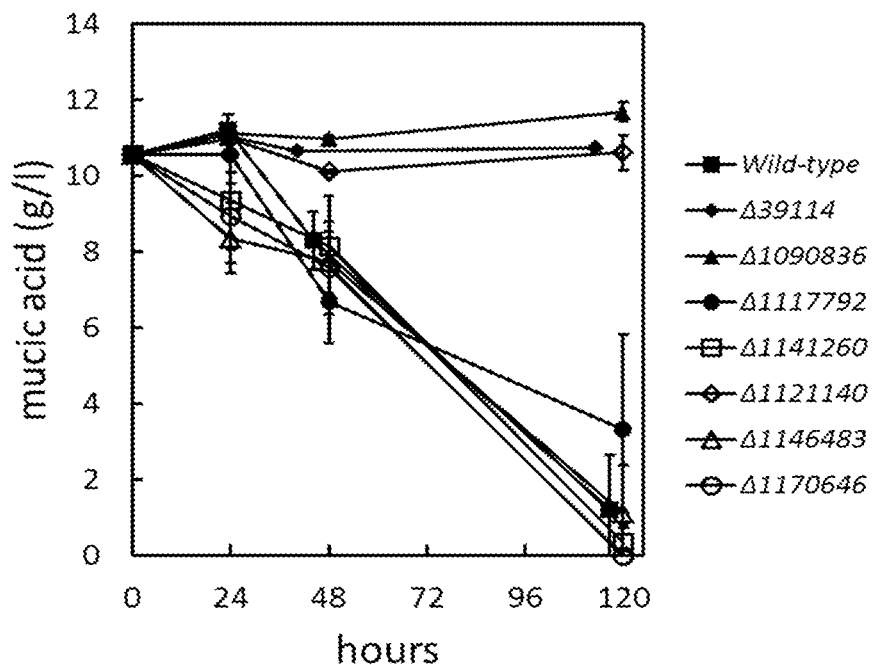
B.
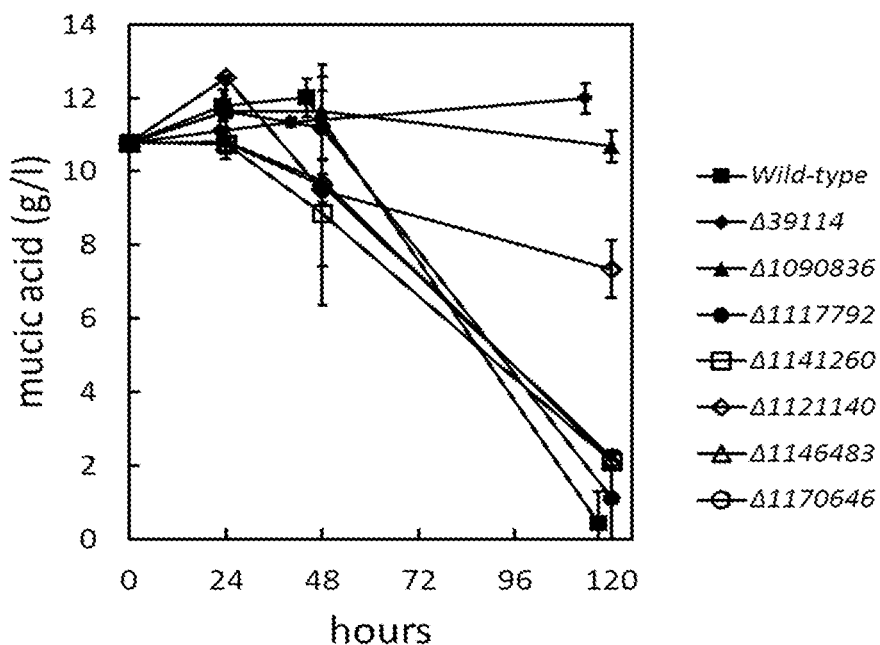
Figures 3A-B.

A.
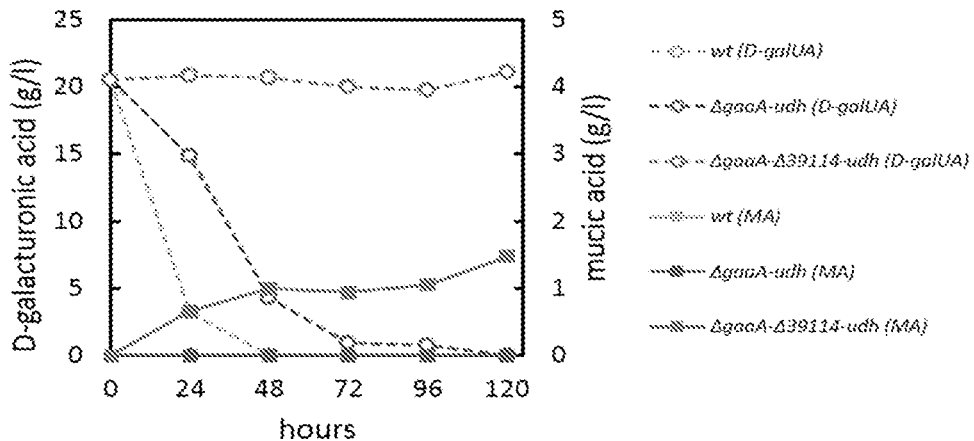
B.
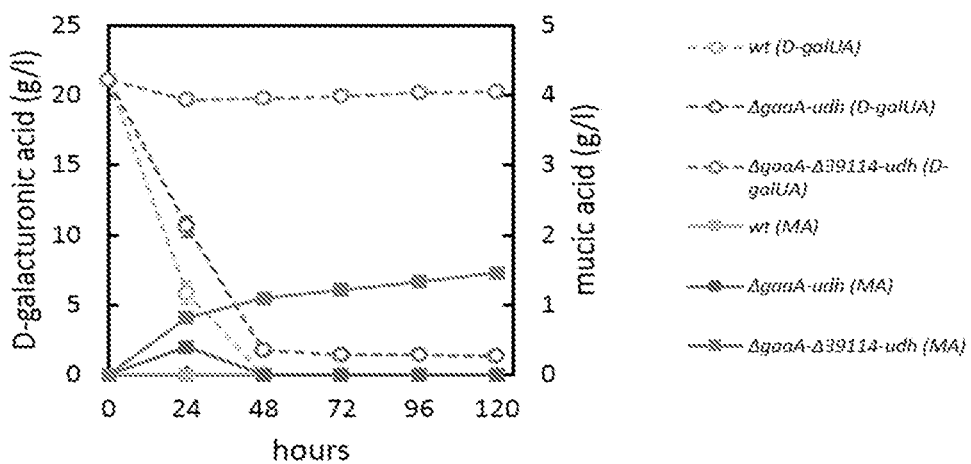
C.
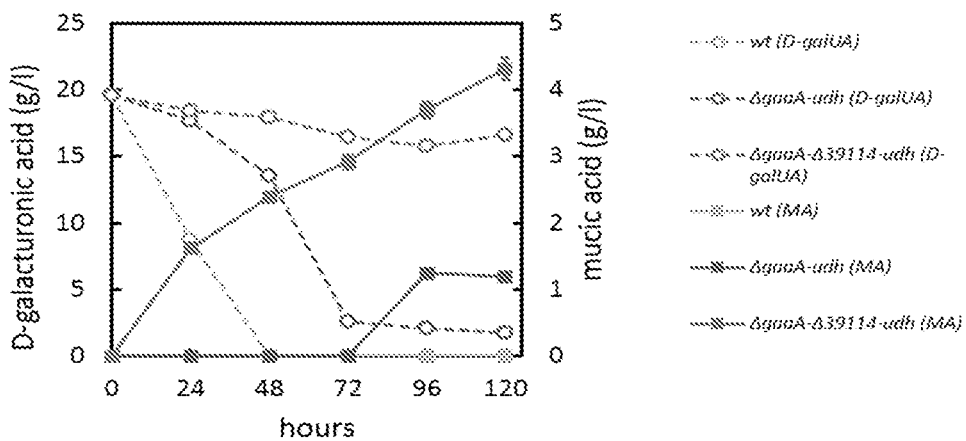
Figures 4A-C.

SEQUENCE LISTING

```
<160> NUMBER OF SEQ ID NOS: 74

<210> SEQ ID NO 1
<211> LENGTH: 68
<212> TYPE: DNA
<213> ORGANISM: Artificial Sequence
<220> FEATURE:
<223> OTHER INFORMATION: primer

<400> SEQUENCE: 1 cccccctcg aggtcgacgg tatcgataag cttgatatcg gcggccgcca cgcgtttcca      60
catcttct                                                              68

<210> SEQ ID NO 2
<211> LENGTH: 60
<212> TYPE: DNA
<213> ORGANISM: Artificial Sequence
<220> FEATURE:
<223> OTHER INFORMATION: primer

<400> SEQUENCE: 2
ctggtatagc caaacatcgc caatcacctc aatcacccgg attagcaatg tgctgcttgc      60

<210> SEQ ID NO 3
<211> LENGTH: 60
<212> TYPE: DNA
<213> ORGANISM: Artificial Sequence
<220> FEATURE:
<223> OTHER INFORMATION: primer

<400> SEQUENCE: 3
gccatgcggg cttgggacgc catgtccgtc gcgtgataac gtgattgcgg aggtgatctg      60

<210> SEQ ID NO 4
```

```
<211> LENGTH: 68
<212> TYPE: DNA
<213> ORGANISM: Artificial Sequence
<220> FEATURE:
<223> OTHER INFORMATION: primer

<400> SEQUENCE: 4
agctccaccg cggtggcggc cgctctagaa ctagtggatc gcggccgcga aactgatcga     60
tcagtcac                                                              68

<210> SEQ ID NO 5
<211> LENGTH: 68
<212> TYPE: DNA
<213> ORGANISM: Artificial Sequence
<220> FEATURE:
<223> OTHER INFORMATION: primer

<400> SEQUENCE: 5
ccccccctcg aggtcgacgg tatcgataag cttgatatcg gcggccgcga cagggttgag     60
ccagtcta                                                              68

<210> SEQ ID NO 6
<211> LENGTH: 60
<212> TYPE: DNA
<213> ORGANISM: Artificial Sequence
<220> FEATURE:
<223> OTHER INFORMATION: primer

<400> SEQUENCE: 6
ctggtatagc caaacatcgc caatcacctc aatcacccgg tgcgactagt tgggtgtcac     60

<210> SEQ ID NO 7
<211> LENGTH: 60
<212> TYPE: DNA
<213> ORGANISM: Artificial Sequence
<220> FEATURE:
<223> OTHER INFORMATION: primer

<400> SEQUENCE: 7
gccatgcggg cttgggacgc catgtccgtc gcgtgataac caggattgta caacttagtt     60

<210> SEQ ID NO 8
<211> LENGTH: 68
<212> TYPE: DNA
<213> ORGANISM: Artificial Sequence
<220> FEATURE:
<223> OTHER INFORMATION: primer

<400> SEQUENCE: 8
agctccaccg cggtggcggc cgctctagaa ctagtggatc gcggccgcgt acatctcagg     60
gtaatatc                                                              68

<210> SEQ ID NO 9
<211> LENGTH: 68
<212> TYPE: DNA
<213> ORGANISM: Artificial Sequence
<220> FEATURE:
<223> OTHER INFORMATION: primer

<400> SEQUENCE: 9
ccccccctcg aggtcgacgg tatcgataag cttgatatcg gcggccgcct acgagccgta     60
gattgcgt                                                              68
```

```
<210> SEQ ID NO 10
<211> LENGTH: 60
<212> TYPE: DNA
<213> ORGANISM: Artificial Sequence
<220> FEATURE:
<223> OTHER INFORMATION: primer

<400> SEQUENCE: 10
ctggtatagc caaacatcgc caatcacctc aatcacccgg atgcatggat gcatggatac     60

<210> SEQ ID NO 11
<211> LENGTH: 60
<212> TYPE: DNA
<213> ORGANISM: Artificial Sequence
<220> FEATURE:
<223> OTHER INFORMATION: primer

<400> SEQUENCE: 11
gccatgcggg cttgggacgc catgtccgtc gcgtgataac cagtcgtgtt aaagcgatcc     60

<210> SEQ ID NO 12
<211> LENGTH: 69
<212> TYPE: DNA
<213> ORGANISM: Artificial Sequence
<220> FEATURE:
<223> OTHER INFORMATION: primer

<400> SEQUENCE: 12
agctccaccg cggtggcggc cgctctagaa ctagtggatc gcggccgcaa ggagcgcgag     60
ggaatcagc                                                             69

<210> SEQ ID NO 13
<211> LENGTH: 67
<212> TYPE: DNA
<213> ORGANISM: Artificial Sequence
<220> FEATURE:
<223> OTHER INFORMATION: primer

<400> SEQUENCE: 13
ccccccctcg aggtcgacgg tatcgataag cttgatatcg gcggccgcga accaggcgca     60
gcggatc                                                               67

<210> SEQ ID NO 14
<211> LENGTH: 60
<212> TYPE: DNA
<213> ORGANISM: Artificial Sequence
<220> FEATURE:
<223> OTHER INFORMATION: primer

<400> SEQUENCE: 14
ctggtatagc caaacatcgc caatcacctc aatcacccgg ctttcttacg acgttgatcc     60

<210> SEQ ID NO 15
<211> LENGTH: 60
<212> TYPE: DNA
<213> ORGANISM: Artificial Sequence
<220> FEATURE:
<223> OTHER INFORMATION: primer

<400> SEQUENCE: 15
gccatgcggg cttgggacgc catgtccgtc gcgtgataac gtcctgtagt agtaggataa     60

<210> SEQ ID NO 16
<211> LENGTH: 68
<212> TYPE: DNA
```

```
<213> ORGANISM: Artificial Sequence
<220> FEATURE:
<223> OTHER INFORMATION: primer

<400> SEQUENCE: 16
agctccaccg cggtggcggc cgctctagaa ctagtggatc gcggccgcgt tgctatcaca    60
aaggattc                                                             68

<210> SEQ ID NO 17
<211> LENGTH: 68
<212> TYPE: DNA
<213> ORGANISM: Artificial Sequence
<220> FEATURE:
<223> OTHER INFORMATION: primer

<400> SEQUENCE: 17
ccccccctcg aggtcgacgg tatcgataag cttgatatcg gcggccgcgt attggcttaa    60
cccaccct                                                             68

<210> SEQ ID NO 18
<211> LENGTH: 60
<212> TYPE: DNA
<213> ORGANISM: Artificial Sequence
<220> FEATURE:
<223> OTHER INFORMATION: primer

<400> SEQUENCE: 18
ctggtatagc caaacatcgc caatcacctc aatcacccgg cgagtgattc ttcgattata    60

<210> SEQ ID NO 19
<211> LENGTH: 61
<212> TYPE: DNA
<213> ORGANISM: Artificial Sequence
<220> FEATURE:
<223> OTHER INFORMATION: primer

<400> SEQUENCE: 19
gccatgcggg cttgggacgc catgtccgtc gcgtgataac cagtaacagt aatcgtagca    60
g                                                                    61

<210> SEQ ID NO 20
<211> LENGTH: 68
<212> TYPE: DNA
<213> ORGANISM: Artificial Sequence
<220> FEATURE:
<223> OTHER INFORMATION: primer

<400> SEQUENCE: 20
agctccaccg cggtggcggc cgctctagaa ctagtggatc gcggccgcac ggcgccaatg    60
agatatgc                                                             68

<210> SEQ ID NO 21
<211> LENGTH: 68
<212> TYPE: DNA
<213> ORGANISM: Artificial Sequence
<220> FEATURE:
<223> OTHER INFORMATION: primer

<400> SEQUENCE: 21
ccccccctcg aggtcgacgg tatcgataag cttgatatcg gcggccgcct aagctttagc    60
tacaagca                                                             68
```

```
<210> SEQ ID NO 22
<211> LENGTH: 60
<212> TYPE: DNA
<213> ORGANISM: Artificial Sequence
<220> FEATURE:
<223> OTHER INFORMATION: primer

<400> SEQUENCE: 22
ctggtatagc caaacatcgc caatcacctc aatcacccgg cgttgttaca tatagaagca      60

<210> SEQ ID NO 23
<211> LENGTH: 60
<212> TYPE: DNA
<213> ORGANISM: Artificial Sequence
<220> FEATURE:
<223> OTHER INFORMATION: primer

<400> SEQUENCE: 23
gccatgcggg cttgggacgc catgtccgtc gcgtgataac gtggtctatg ttggatagat      60

<210> SEQ ID NO 24
<211> LENGTH: 68
<212> TYPE: DNA
<213> ORGANISM: Artificial Sequence
<220> FEATURE:
<223> OTHER INFORMATION: primer

<400> SEQUENCE: 24
agctccaccg cggtggcggc cgctctagaa ctagtggatc gcggccgctc ccagtcctca      60
tcatcatc                                                              68

<210> SEQ ID NO 25
<211> LENGTH: 68
<212> TYPE: DNA
<213> ORGANISM: Artificial Sequence
<220> FEATURE:
<223> OTHER INFORMATION: primer

<400> SEQUENCE: 25 cccccctcg aggtcgacgg tatcgataag cttgatatcg gcggccgccg accgatggac       60
actcttgt                                                              68

<210> SEQ ID NO 26
<211> LENGTH: 60
<212> TYPE: DNA
<213> ORGANISM: Artificial Sequence
<220> FEATURE:
<223> OTHER INFORMATION: primer

<400> SEQUENCE: 26
ctggtatagc caaacatcgc caatcacctc aatcacccgg tgtaggcaaa gggtgagagt      60

<210> SEQ ID NO 27
<211> LENGTH: 60
<212> TYPE: DNA
<213> ORGANISM: Artificial Sequence
<220> FEATURE:
<223> OTHER INFORMATION: primer

<400> SEQUENCE: 27
gccatgcggg cttgggacgc catgtccgtc gcgtgataac cattggcttc gcgctgaaat      60

<210> SEQ ID NO 28
<211> LENGTH: 68
<212> TYPE: DNA
```

<213> ORGANISM: Artificial Sequence
<220> FEATURE:
<223> OTHER INFORMATION: primer

<400> SEQUENCE: 28
agctccaccg cggtggcggc cgctctagaa ctagtggatc gcggccgcgc aaagcagacg    60
ttaagccc                                                             68

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
agctggtata gccaaacatc                                                20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gctaatacgt ggtatgtatg                                                20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gaaggcagga ttggagaagg                                                20

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
cacgtgctac gccaggtac                                                 19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gtagcatgga ggtaaagtat                                                20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34

```
cagctatgct acagtatatc                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
caagctacta tcgagcactc                                              20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gtagactacc aagtcgtagt                                              20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ttgagctcgt gtgtctggac                                              20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
acagcggcta gataacgagc                                              20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gatacatggg cagcgatgga                                              20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ctctcctcac ccacctctga                                              20

<210> SEQ ID NO 41
<211> LENGTH: 20
<212> TYPE: DNA
```

```
<213> ORGANISM: Artificial Sequence
<220> FEATURE:
<223> OTHER INFORMATION: primer

<400> SEQUENCE: 41
atgaccatca ccgaacccac                                              20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ggctcgcgca aactgaatag                                              20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
caaggtcatc gtcgcggata                                              20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ccaacggcac atttccgatg                                              20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gcatagcagt gcttcttcgc                                              20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ctccgttgtt cactccgtca                                              20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
gctggctttt cgtcaaggtg                                              20
```

```
<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gcttgatagc ttcggggtgt                                                 20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gcccataatc ctccacctcg                                                 20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
cagtcaacgg acaatgcacc                                                 20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cccctatacc cgtctgtttg                                                 20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ccatggcatc ctcgagctcc                                                 20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gttgttcatc gattccccg                                                  20

<210> SEQ ID NO 54
<211> LENGTH: 20
<212> TYPE: DNA
<213> ORGANISM: Artificial Sequence
<220> FEATURE:
```

<223> OTHER INFORMATION: primer

<400> SEQUENCE: 54
catcctcgac tgcagcaatg                                           20

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
cgtactgtca gagcaaccga                                           20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56 ccggggtaa tagtagtcgc                                            20

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
gtgctcttct aggttccgag                                           20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
ggcggcaccg tccgtgtgtg                                           20

<210> SEQ ID NO 59
<211> LENGTH: 20
<212> TYPE: DNA
<213> ORGANISM: Artificial Sequence
<220> FEATURE:
<223> OTHER INFORMATION: protospacer sequence

<400> SEQUENCE: 59
tatcacctcc gcataaccat                                           20

<210> SEQ ID NO 60
<211> LENGTH: 20
<212> TYPE: DNA
<213> ORGANISM: Artificial Sequence
<220> FEATURE:
<223> OTHER INFORMATION: protospacer sequence

<400> SEQUENCE: 60
agttcagtct ctgtggagga                                           20

<210> SEQ ID NO 61
<211> LENGTH: 20
<212> TYPE: DNA
<213> ORGANISM: Artificial Sequence
<220> FEATURE:
<223> OTHER INFORMATION: protospacer sequence

<400> SEQUENCE: 61
atgcatccat tttagagcca                                              20

<210> SEQ ID NO 62
<211> LENGTH: 20
<212> TYPE: DNA
<213> ORGANISM: Artificial Sequence
<220> FEATURE:
<223> OTHER INFORMATION: protospacer sequence

<400> SEQUENCE: 62
tctggaagtc gctgtgccct                                              20

<210> SEQ ID NO 63
<211> LENGTH: 20
<212> TYPE: DNA
<213> ORGANISM: Artificial Sequence
<220> FEATURE:
<223> OTHER INFORMATION: protospacer sequence

<400> SEQUENCE: 63
tatcgccaga acaaaaagcg                                              20

<210> SEQ ID NO 64
<211> LENGTH: 20
<212> TYPE: DNA
<213> ORGANISM: Artificial Sequence
<220> FEATURE:
<223> OTHER INFORMATION: protospacer sequence

<400> SEQUENCE: 64
agaccgatca ttattgacga                                              20

<210> SEQ ID NO 65
<211> LENGTH: 20
<212> TYPE: DNA
<213> ORGANISM: Artificial Sequence
<220> FEATURE:
<223> OTHER INFORMATION: protospacer sequence

<400> SEQUENCE: 65
tcgtgtctga cattccacaa                                              20

<210> SEQ ID NO 66
<211> LENGTH: 20
<212> TYPE: DNA
<213> ORGANISM: Artificial Sequence
<220> FEATURE:
<223> OTHER INFORMATION: protospacer sequence

<400> SEQUENCE: 66
acagagttct attcacgggt                                              20

<210> SEQ ID NO 67
<211> LENGTH: 20
<212> TYPE: DNA
<213> ORGANISM: Artificial Sequence
<220> FEATURE:
<223> OTHER INFORMATION: protospacer sequence

```
<400> SEQUENCE: 67 tgttacccccc acgcggggta                                          20

<210> SEQ ID NO 68
<211> LENGTH: 20
<212> TYPE: DNA
<213> ORGANISM: Artificial Sequence
<220> FEATURE:
<223> OTHER INFORMATION: protospacer sequence

<400> SEQUENCE: 68
agacttgtag gccaggatgt                                           20

<210> SEQ ID NO 69
<211> LENGTH: 20
<212> TYPE: DNA
<213> ORGANISM: Artificial Sequence
<220> FEATURE:
<223> OTHER INFORMATION: protospacer sequence

<400> SEQUENCE: 69
aggcaaaggg tgagagtagt                                           20

<210> SEQ ID NO 70
<211> LENGTH: 20
<212> TYPE: DNA
<213> ORGANISM: Artificial Sequence
<220> FEATURE:
<223> OTHER INFORMATION: protospacer sequence

<400> SEQUENCE: 70
agctcccccc tgcctcctcg                                           20

<210> SEQ ID NO 71
<211> LENGTH: 20
<212> TYPE: DNA
<213> ORGANISM: Artificial Sequence
<220> FEATURE:
<223> OTHER INFORMATION: protospacer sequence

<400> SEQUENCE: 71
tccacgatgc cctacacacc                                           20

<210> SEQ ID NO 72
<211> LENGTH: 1006
<212> TYPE: PRT
<213> ORGANISM: Trichoderma reesei

<400> SEQUENCE: 72
```

Met Leu Ser Thr Ile Ala Pro Gln Pro Thr Leu Gln Glu Pro Leu
1               5                   10                  15

Ser Lys Asp Asp His Ile Leu Pro Leu Gln Ser Tyr Glu Pro Ser Thr
            20                  25                  30

Ile Asp Glu Leu Val Arg Gln Arg Ala Ser Leu Gly Ala Ala Gln Pro
        35                  40                  45

Ile Ile Ser Tyr Pro Arg Thr Gly Ile Glu Tyr Val Asp Tyr Pro Leu
    50                  55                  60

Gln Gln Leu Asp Val Phe Ala Phe Arg Val Ser Lys Val Leu Ser Asp
65                  70                  75                  80

Arg Ile Pro Pro Arg Lys Ser Ser Ala Glu Thr Pro Lys Val Ile Ala
                85                  90                  95

Leu Leu Gly Pro Ser Asp Leu Asn Tyr Leu Val Met Leu Leu Ser Leu

-continued

```
                    100                 105                 110
Ala Lys Leu Ser His Ser Gly Leu Leu Ser Thr Arg Ile Ser Ile
                115                 120                 125

Asp Ala Tyr Val Ser Leu Leu Glu Arg Thr Gly Ser Arg His Val Phe
            130                 135                 140

Ile His Ser Ser Phe Arg Asp Thr Ala Glu Glu Ile Lys Lys Arg Val
145                 150                 155                 160

Pro Glu Leu Val Ile Asp Glu Ile Pro Thr Glu Glu Asn Tyr His Tyr
                165                 170                 175

Pro Ile Thr Glu Tyr Val Asp Thr Asn Leu Val Pro His Leu Asp Pro
                180                 185                 190

Lys Ile Glu Ser Lys His Ile Ala Trp Ile Ile His Ser Ser Gly Ser
                195                 200                 205

Thr Gly Leu Pro Lys Pro Ile Phe His Thr Gln Ser Ala Ala Leu Lys
            210                 215                 220

Asn Tyr Ser Gly His Met Asn Met Ser Gly Phe Val Thr Leu Pro Leu
225                 230                 235                 240

Tyr His Asn His Gly Ile Ser Cys Leu Phe Arg Thr Ile His Ala Ser
                245                 250                 255

Lys Gln Leu His Leu Tyr Asn Ala Asn Leu Pro Leu Thr Arg Gln Tyr
                260                 265                 270

Leu Leu Glu Ile Met Gly Ser Asn Ser Phe Glu Val Phe Tyr Gly Val
                275                 280                 285

Pro Tyr Ala Leu Lys Leu Leu Ala Glu Thr Arg Glu Gly Ile Ser Ala
            290                 295                 300

Leu Ala Lys Leu Lys Ala Val Met Phe Gly Gly Ser Ala Cys Pro Asp
305                 310                 315                 320

Ser Leu Gly Asn Leu Leu Val Glu Asn Asp Val His Leu Ile Ser His
                325                 330                 335

Tyr Gly Ser Thr Glu Thr Gly Gln Leu Met Met Ser Thr Arg Pro Arg
            340                 345                 350

Asp Asp Lys Gly Trp Asp Trp Leu Arg Pro Ser Asp Thr Val Lys Arg
                355                 360                 365

Phe Leu Arg Phe Glu Glu Arg Phe Pro Gly Val Phe Glu Leu Val Cys
            370                 375                 380

Leu Asp Gly Trp Pro Ser Lys Val Met Thr Asn Arg Pro Asp Gly Ser
385                 390                 395                 400

Tyr Ala Thr Lys Asp Leu Phe Val Lys His Pro Thr Met Glu Ala Tyr
                405                 410                 415

Lys Tyr Tyr Ala Arg Leu Asp Asp Thr Ile Val Leu Tyr Asn Gly Glu
            420                 425                 430

Lys Val Asn Pro Leu Asp Leu Glu Gly Arg Val Arg Gln Arg Ser Thr
            435                 440                 445

Val Ala Glu Ala Ile Ala Phe Gly Ala Gly Lys Ala His Ile Gly Leu
            450                 455                 460

Ala Val Ile Arg Ala Pro Gly Thr Glu Ser Leu Ser Asp Glu Asp Ile
465                 470                 475                 480

Ile Asp Ser Ile Trp Pro Ala Val Glu Lys Ala His Glu Ala Leu Pro
                485                 490                 495

Ala Phe Gly Gln Leu Ser Lys Asn Met Val Arg Val Leu Pro Ala Asp
                500                 505                 510

Thr Pro Tyr Pro Arg Thr Asp Lys Gly Thr Ile Ile Arg Gln Ala Phe
                515                 520                 525
```

```
Tyr Lys Asn Phe Gln Pro Leu Ile Glu Glu Val Tyr Ala Ala Val Asp
    530                 535                 540

Ala Met Thr Gly Thr Leu Val Leu Ser Glu Pro Glu Leu Arg Asp Phe
545                 550                 555                 560

Leu Lys Lys Gln Leu Leu Gln Ile Leu Pro Leu Lys Asp Ser Asn Leu
                    565                 570                 575

Leu Thr Asp Asp Ala Asp Phe Phe Ser Leu Gly Met Asp Ser Leu Gln
                580                 585                 590

Ala Ser Gln Leu Arg Ser Ile Leu Val Gln Asn Leu Asp Thr Lys Gly
            595                 600                 605

His Gln Leu Gly Leu Asn Ile Ala Phe Glu Gln Pro Thr Ile Ser Leu
    610                 615                 620

Leu Ala Arg Tyr Leu Ala Ala Val Gln Ser Gly Glu Ala Leu Pro Gly
625                 630                 635                 640

Ser Gln Pro Ile His Glu Gln Met Arg Ala Leu Ile Ser Gln Phe Ser
                    645                 650                 655

His Phe Glu Pro His Val Pro His Ser Asn Glu Leu Pro Gly Arg Tyr
                660                 665                 670

Val Val Ser Ile Pro Gln His Pro Gly Ser His Arg Pro Leu Ser Ser
            675                 680                 685

Ser Ser Lys Ala Lys Leu Ile Ala Leu Pro Ala Pro Thr Leu Ser His
    690                 695                 700

Pro Thr Leu Ser Leu Pro Glu Glu Thr Tyr Asn Thr Leu Leu Thr Glu
705                 710                 715                 720

Thr Thr Asp Ile Ile His Cys Ala Trp Pro Val Asn Phe Asn Leu Gln
                    725                 730                 735

Leu Ser Ser Leu Ala Gln Asp Thr Leu Pro Thr Leu His Asn Leu Leu
                740                 745                 750

Ser Leu Ala Leu Lys Ala Gln Arg Pro Glu Pro Ala Thr Phe Asn Phe
            755                 760                 765

Cys Ser Ser Val Ser Ser Val Val Asn Ser Ala Val Ser Pro Ile Pro
    770                 775                 780

Glu Thr Leu Pro Glu Ser Leu Thr Ala Ala Gln Ser Met Gly Tyr Ala
785                 790                 795                 800

Gln Ser Lys Leu Ile Ala Glu His Ile Cys Ala Asn Ala Thr Pro Tyr
                    805                 810                 815

Leu Asp Ala Arg Val Leu Arg Ile Gly Gln Ile Ile Gly Asp Thr Lys
                820                 825                 830

His Gly Val Trp Asn Ala Thr Glu Ala Ile Pro Leu Met Leu Arg Ala
            835                 840                 845

Ala Val Thr Val Gly Ala Leu Pro Arg Leu Asp Glu Arg Met Arg Trp
850                 855                 860

Val Pro Val Asp Val Val Ala Ala Val Met Asp Ile Thr Leu His
865                 870                 875                 880

Lys Glu Glu Gln Gly Leu Glu Arg Lys Lys Gly Ala Asp Asp Val Glu
                    885                 890                 895

Val Tyr Asn Ile Leu Asn Pro Tyr Ser Phe His Trp Thr Lys Asp Leu
                900                 905                 910

Leu Pro Ala Leu Arg Ala Ala Gly Phe Gly Phe Glu Asp Met Glu Phe
            915                 920                 925

Ala Glu Trp Ile Lys Arg Val Lys Asp Leu Ala Asp Pro Glu Arg Asn
930                 935                 940
```

```
Pro Pro Val Lys Leu Val Gly Phe Trp Glu Gly Lys Tyr Gly Ser Ala
945                 950                 955                 960

Lys Pro Phe Arg Gly Leu Glu Phe Val Thr Glu Lys Ala Arg Glu Arg
            965                 970                 975

Ala Glu Gly Leu Arg Glu Leu Ser Ala Glu Gly Leu Glu Gly Gly Leu
                980                 985                 990

Val Gly Lys Met Val Glu Trp Phe Arg Asp Val Ala Trp Val
            995                 1000                1005
```

<210> SEQ ID NO 73
<211> LENGTH: 345
<212> TYPE: PRT
<213> ORGANISM: Trichoderma reesei

<400> SEQUENCE: 73

```
Met Ala Leu Asn Arg Thr Phe Lys Leu Asn Thr Gly Tyr Asp Met Pro
1               5                   10                  15

Ala Val Gly Leu Gly Thr Trp Gln Ser Lys Lys Asp Glu Val Arg Asp
            20                  25                  30

Ala Val Ile Ala Ala Leu Lys Cys Gly Tyr Arg His Ile Asp Ala Ala
        35                  40                  45

Ala Val Tyr Gly Asn Glu Gln Glu Val Gly Asp Gly Met Arg Leu Ser
    50                  55                  60

Gly Val Pro Arg Glu Glu Ile Phe Leu Thr Ser Lys Leu Trp Asn Thr
65                  70                  75                  80

His His His Pro Glu Asn Val Glu Glu Ala Val Asp Lys Ser Leu Ala
                85                  90                  95

Asp Leu Gln Thr Asp Tyr Leu Asp Leu Tyr Leu Ile His Trp Pro Val
            100                 105                 110

Ala Phe Arg Tyr Ser Thr Thr Thr Ile Gln Pro Val Asn Glu Gln Thr
        115                 120                 125

Gly Leu Ile Asp Val Val Asp Val Pro Ile Lys Asp Thr Trp Ala Ala
    130                 135                 140

Met Glu Lys Leu Val Glu Lys Gly Lys Val Arg Ser Ile Gly Val Ser
145                 150                 155                 160

Asn Phe Thr Arg Glu Lys Ile Glu Glu Leu Leu Lys Thr Ala Lys Ile
                165                 170                 175

Thr Pro Ala Val Asn Gln Ile Glu Ala His Pro Phe Leu Gln Gln Arg
            180                 185                 190

Asp Leu Leu Glu Trp Ser Thr Gln Lys Gly Ile Val Val Ala Gly Tyr
        195                 200                 205

Ser Pro Leu Gly Asn Asn Ile Tyr Asn Ile Pro Arg Ala Val Asp Asp
    210                 215                 220

Pro Leu Val Ile Glu Thr Ala Lys Lys Leu Asn Lys Thr Pro Ala Gln
225                 230                 235                 240

Val Leu Ile Ser Trp Ala Val Gln Arg Gly Thr Val Val Leu Pro Lys
                245                 250                 255

Ser Val Thr Pro Glu Arg Ile Glu Ser Asn Phe Gln Gly Ser Leu Ser
            260                 265                 270

Pro Thr His Asn Ile Cys Pro His Cys Ala Asn Met Asp Tyr Ser Asp
        275                 280                 285

Phe Val Leu Pro Asp Asp Ala Phe Ser Thr Ile Gln Ser Leu Glu Arg
    290                 295                 300

His Gln Arg Met Asn Phe Pro Ala Arg Ile Gly Val Asp Ile Phe Ser
305                 310                 315                 320
```

Glu Val Gly Glu Ser Val Arg Lys Ser Ala Leu Ala Trp Ala Glu
            325                 330                 335

Gln Gln Arg Val Leu Lys Ala Lys Ala
            340                 345

<210> SEQ ID NO 74
<211> LENGTH: 783
<212> TYPE: PRT
<213> ORGANISM: Trichoderma reesei

<400> SEQUENCE: 74

Met Gly Ser Ser Leu Ser Ser Val Ser Asn Ser Ser Thr Glu Asp Ile
1               5                   10                  15

Val Ile Val Gly Ala Gly Ala Ser Gly Ile Ala Val Leu Leu Arg Leu
            20                  25                  30

Ile Glu His Ala Lys Asp Gly Lys Lys Ile Pro Pro Ile Val Val
            35                  40                  45

Glu Lys Ala Ser Pro Pro Gly Pro Gly Leu Ala Tyr Ser Ala Ala Cys
50                  55                  60

Thr Gly Thr Ile Leu Asn Met His Thr Asp Thr Met Gly Leu Tyr Tyr
65                  70                  75                  80

Asn Asp Pro Lys His Phe Thr Arg Trp Arg Ser Glu Leu Ala Ser Gly
                85                  90                  95

Pro Phe Pro Ser Arg Ser Gln Tyr Gly Glu Tyr Leu Glu Ala Met Trp
            100                 105                 110

Ser Glu Ile Leu Ser Gln Ala Gln Gln Met Gly Leu Asp Ile Ser Ile
            115                 120                 125

Ile Gln Asp Glu Val Ser Asp Ile Asp Arg His Asp Asp Ser Thr Phe
        130                 135                 140

Thr Leu Thr Leu Thr Gly Gly Arg Arg Leu Ala Ala Gln Ser Val Val
145                 150                 155                 160

Leu Ala Leu Gly Asn Tyr Thr Ser Thr Leu Asn Thr His Leu Leu Asn
                165                 170                 175

Gln Pro Gly Phe Phe Pro Ser Pro Trp Pro Thr Ser Gln Leu Lys Thr
            180                 185                 190

Ile Pro Ala Asp Ala Ser Val Leu Ile Ile Gly Ser Arg Leu Ser Ala
            195                 200                 205

Val Asp Ala Ala Leu Phe Leu Ser Lys Asn Gly His Lys Gly Pro Leu
        210                 215                 220

Thr Phe Met Ser Arg Ser Gly Arg Leu Pro Lys Val Gln Gly Glu Pro
225                 230                 235                 240

Glu Pro Tyr Pro Arg Arg Tyr Thr Leu His Thr Leu Ala Arg Tyr Ile
                245                 250                 255

Glu Ser Asn Pro Ala Asp Gly Leu Val Lys Leu Thr Thr Leu Met
            260                 265                 270

Asp Glu Ile Asp Gly Val Asn Asn Gly Asp Trp Thr Trp Ile Gln Lys
        275                 280                 285

His Ala Ser Pro Leu Ala Glu Leu Arg Ala Asp Leu Phe Ala Ala Gln
290                 295                 300

Gly Gly Asn Val His Trp Gln Thr Val Leu Arg His Thr Ala Pro Val
305                 310                 315                 320

Ile Glu Arg Tyr Trp His Cys Leu Pro Leu Glu Ser Gln Lys Leu Phe
                325                 330                 335

Met Ala Lys Phe Phe Thr Pro Trp Met Arg Tyr Arg His Gly Met Pro

-continued

```
                340             345             350
Val Gln Asn Ala Gln Lys Ile Leu Asn Leu Met Glu Thr Ser Gln Leu
            355                 360                 365
Ser Val Val Ala Gly Glu Ala Val His Trp Asp Glu Gly Glu Gly Ala
        370                 375                 380
Phe Ile Ala Gln Thr Thr Ser Gly Pro Ile Glu Ala Ser Tyr Val Ile
385                 390                 395                 400
Glu Ala Thr Gly Gln Glu Ser His Leu Asp Arg Ile Pro Ser Pro Leu
                405                 410                 415
Val Gln Ser Ala Val Arg Lys Gly Leu Phe Thr Pro His Pro Met Gly
            420                 425                 430
Gly Val Asp Val Asp Phe His Thr Leu Cys Thr Ser Thr Pro Gly Leu
        435                 440                 445
Tyr Thr Met Gly Ser Leu Thr Arg Gly Thr His Phe Tyr Val Ser Ala
    450                 455                 460
Ile Asp Arg Thr Ala Ala His Ala Ala Arg Ile Ala Asp Ala Leu Val
465                 470                 475                 480
Gly Glu Pro Pro Ala Arg Pro Val His Ile Ala Ile Phe Leu Gly Ala
                485                 490                 495
Asp Val Ala Ser His Leu Ile Ala Ser Asp Leu Val Pro Leu Leu Leu
            500                 505                 510
Ala Glu Gly His Met Pro Phe Leu Phe Leu Ser Ser Ser Lys Gln Thr
        515                 520                 525
Pro Ser Leu Glu Gly Ser Asp Ser Arg Pro Phe Asp Leu Arg Lys Leu
    530                 535                 540
Glu Phe Phe Glu Arg Glu Leu Phe Arg Lys His Leu Cys Pro Arg Leu
545                 550                 555                 560
Lys Glu His Ser Phe Lys Gly Ala Arg His Met Thr Val Glu Gln Met
                565                 570                 575
Gln Thr Ala Tyr Gly Val Leu Val Gln Glu Ile Pro Asp Thr Lys Gly
            580                 585                 590
Ala Ser Val Gly Arg Met Leu Gln Lys Tyr Phe Ile Asp Val Gly Ile
        595                 600                 605
Ser Leu Thr Cys Ala Glu Ala Pro Asp Gln Asp Val Ile Ala Tyr Leu
    610                 615                 620
Ser Ser Ser Ser Arg His Leu Leu Ala Val Asp Ala Gly Val Leu Ser
625                 630                 635                 640
Ala Pro Trp Asp Ser Lys Lys Ala Gly Ala Lys Phe Gly Tyr Thr Leu
                645                 650                 655
Arg Glu Phe His Glu Asp Gly Lys Leu Gly Asp Val Ile Asp Arg Arg
            660                 665                 670
Thr Ile Pro Val Gly Glu Ser Ala Ala Met Leu Thr Gly Val Gly Lys
        675                 680                 685
Glu Tyr Ala Leu Gly Val Gln Met Ala Val Asp Ala Ile Lys Leu Val
    690                 695                 700
Ser Arg Gly Lys Pro Leu Ser Asp Val Ala Cys Pro Arg Ser Ser Asp
705                 710                 715                 720
Thr Ser Arg His Cys Tyr Leu Ser Ala Glu Glu Leu Trp Lys Tyr Cys
                725                 730                 735
His Glu Arg Arg Ile Glu Leu Val Asp Asp Lys Arg Val Val Glu Met
            740                 745                 750
Leu Val Glu Ser Phe Ala Pro Leu Glu Lys Arg Glu Val Leu Arg Lys
        755                 760                 765
```

```
Glu Leu Asp Glu Ala Val Gln Glu Trp Tyr Val Lys Gln Glu Val
    770                 775                 780
```

METHOD FOR PRODUCING MESO-GALACTARIC ACID BY CONTACTING A FUNGAL CELL WITH A BIOMATERIAL HAVING GALACTURONIC ACID

This application is the U.S. national phase of International Application No. PCT/FI2017/050378 filed May 19, 2017 which designated the U.S. and claims priority to FI Patent Application No. 20165425 filed May 20, 2016, the entire contents of each of which are hereby incorporated by reference.

FIELD OF THE INVENTION

The present invention relates to a field of genetically modified fungal cells and converting galacturonic acid to meso-galactaric acid, more precisely to a method of producing meso-galactaric acid. The invention further relates to recombinant fungal cells having a specific combination of modifications including but not limited to expression of uronate dehydrogenase enzyme, reduced D-galacturonic acid reductase activity, and furthermore reduced meso-galactaric acid catabolism, as well as uses and methods related thereto.

BACKGROUND OF THE INVENTION meso-Galactaric acid, also known as mucic acid or galactaric acid, is an aldaric acid having terminal carboxylic acid groups. In nature, it occurs as a metabolite in the bacterial oxidative catabolic pathway for D-galacturonic acid which produces α-ketoglutarate, an intermediate of TCA cycle, as final product (Chang and Feingold, 1970; Dagley and Trudgill, 1965). In the pathway, an uronate dehydrogenase (UDH) oxidizes D-galacturonic acid resulting in formation of galactaro-1,4-lactone (FIG. 1). After the spontaneous or enzymatic hydrolysis of the lactone, meso-galactaric acid is formed. D-Galacturonic acid in turn is the most abundant monomer in pectin. Pectin is a component of plant primary cell wall and especially abundant in non-woody plant biomass such as in fruit peels. Several pectin-rich waste biomass streams, such as residues from citrus fruit and sugar beet processing are available and currently poorly utilized.

As a dicarboxylic acid, meso-galactaric acid is an attractive renewable alternative to be used as a platform chemical in polymers. It can be, for instance, chemically reduced to adipic acid or 2,5-furandicarboxylic acid (FDCA). Adipic acid has a huge market and it is widely used as a precursor in polymers such as nylon. FDCA is considered as promising renewable replacement for the fossil-based terephthalic acid that is used e.g. in PET plastic.

Production of meso-galactaric acid from D-galacturonic acid via chemical (Rautiainen et al., 2015) or biochemical (Benz et al., 2014; Mojzita et al., 2010) oxidation has been described in the literature. In addition, a combined process was recently reported including enzymatic hydrolysis of pectin, oxidation of resulting D-galacturonic acid to meso-galactaric acid by engineered *E. coli* and chemical reduction of meso-galactaric acid to adipic acid (H. Zhang et al., 2016). In the biochemical route, the filamentous fungus *Trichoderma reesei* was recently engineered for meso-galactaric acid production by disrupting the homologous D-galacturonic acid catabolism and introducing a heterologous UDH from the bacterial oxidative pathway (Mojzita et al., 2010; WO2010/072902 (A1)). The same strategy was also tested with *Aspergillus niger* that is, in contrast to *T. reesei*, efficient in pectin hydrolysis allowing a consolidated bioprocessing of pectin rich biomass (Kuivanen et al., 2014). However, expression of UDH in *A. niger* did not result in efficient meso-galactaric acid production.

Therefore, a need still exists for micro-organisms, specifically fungal cells, having ability to effectively produce meso-galactaric acid. The present invention improves the biochemical production of meso-galactaric acid in recombinant micro-organisms.

Brief Description of the Invention

An object of the present invention is to provide methods and means for converting inexpensive pectin rich biomass such as sugar beet pulp or citrus processing waste, CPW, to galactarate and furthermore providing dicarboxylic acid, namely mucic acid i.e. meso-galactaric, for e.g. polymer industry.

More specifically an object of the present invention is to provide a method to solve the problems of time consuming, expensive and inefficient production of meso-galactaric acid. In the present invention the pectin rich biomass is converted in a single fermentative process to the desired product, thus taking into account both ecological compatibility and sustainable development issues.

The objects of the invention are achieved by a method and an arrangement, which are characterized by what is stated in the independent claims. The specific embodiments of the invention are disclosed in the dependent claims.

The present invention provides a method and genetically modified fungal cells for production of meso-Galactaric acid from D-galacturonic acid or galacturonate (i.e. any salt or ester of galacturonic acid) by utilizing very specific combinations of genetic modifications.

Surprisingly, the present invention is able to overcome the drawbacks of the prior art e.g. the problem that galactarates are catabolized in some microorganisms, specifically fungi. The present invention provides a way to stop the galactarate catabolism. Indeed, one benefit of this invention is that fungal cells may be utilized for meso-galactaric acid production. Fungi are especially efficient in producing pectinases for the hydrolysis of the pectin in pectin rich biomass. The pectinases hydrolyse the pectin to produce galacturonate, the substrate for the production of galactarate. The present invention enables production of galactarate from pectin rich biomass, by just applying some spores of the engineered fungus to e.g. citrus peels. The following autonomous fermentation process will convert it to the desired product galactarate.

Also, by the present invention it is possible to identify genes that are essential for galactarate catabolism. One or more said genes may be e.g. inhibited or knocked out. The resulting fungal strain is now able to catabolize galactarate. The resulting strain is converting galacturonate to galactarate but is not catabolizing galactarate.

In one aspect, the present invention relates to a method for producing meso-galactaric acid, said method comprising contacting a fungal cell genetically modified to express uronate dehydrogenase enzyme, genetically modified to have reduced D-galacturonic acid reductase activity, and modified to reduce meso-galactaric acid catabolism, with a biomaterial comprising galacturonic acid, and recovering the resulting meso-galactaric acid.

In another aspect, the present invention relates to a fungal cell that has been genetically modified to express uronate dehydrogenase enzyme, genetically modified to have reduced D-galacturonic acid reductase activity, and is capable of converting D-galacturonic acid to meso-galactaric acid, wherein said fungal cell has been further modified to reduce meso-galactaric acid catabolism.

Further, the present invention relates to a method for treating biomaterial comprising galacturonic acid, which method comprises that a fungal cell genetically modified to express uronate dehydrogenase enzyme, genetically modified to have reduced D-galacturonic acid reductase activity, and modified to reduce meso-galactaric acid catabolism, is contacted with said biomaterial under suitable culture conditions.

Still, a further aspect of the present invention relates to use of the fungal cell of the present invention for producing meso-galactaric acid from pectin.

Still, a further aspect of the present invention relates to a method of preparing a fungal cell, said method comprising transforming a fungal cell with at least one polynucleotide encoding uronate dehydrogenase enzyme for enhanced expression of said polynucleotide, and reducing D-galacturonic acid reductase activity and meso-galactaric acid catabolism.

Still further, one aspect of the present invention relates to a method for identifying a polynucleotide or polypeptide of the meso-galactaric acid catabolic pathway, wherein the method comprises contacting a wild type fungal cell with meso-galactaric acid, carrying out a transcriptional analysis on a sample obtained from the wild type fungal cell contacted with meso-galactaric acid, and identifying overexpressed polynucleotides compared to a sample obtained from a wild type fungal cell not contacted with meso-galactaric acid.

By the present invention the catabolism of meso-galactaric was disrupted and a fungal strain capable of meso-galactaric production was generated.

The consolidated process from pectin-rich biomass for the production was also demonstrated.

BRIEF DESCRIPTION OF THE DRAWINGS

In the following the invention will be described in greater detail by means of specific embodiments with reference to the attached drawings, in which

FIG. 3 shows consumption of meso-galactaric acid in liquid cultivations on 24-well plates in (A) minimal medium with D-xylose and (B) YP-medium. Data represent means ± standard deviation from four replicates.

FIG. 4 shows production of meso-galactaric acid (MA, squares) from D-galacturonic acid (D-galUA, open circles) in shake flask cultivations on (A) minimal medium with D-galacturonic acid, (B) minimal medium with D-xylose and D-galacturonic acid and (C) YP-medium with D-galacturonic acid. The strains are wild type (light grey symbols), ΔgaaA-udh (black symbols) and ΔgaaA-Δ39114-udh (grey symbols). Data represent means±standard deviation from three replicates. If error bars are not visible they are smaller than the symbol.

DETAILED DESCRIPTION OF THE INVENTION

Galacturonic acid in pectin-rich residues can be converted to useful compounds exploiting microorganisms. In the present invention, the catabolism of meso-galactaric acid was disrupted in a fungal cell together with at least disrupted endogenous D-galacturonic acid catabolism and expression of uronate dehydrogenase enzyme.

Pectin is structurally the most complex family of polysaccharides in nature and it can be found in plant cell walls. Pectin consist of a α-1,4-linked D-galacturonic acid backbone with sugar side chains. Approximately 70% of pectin mass is made up of galacturonic acid. There are five different types of pectin classified based on their structure: homogalacturonan (HG), xylogalacturonan (XGA), apiogalacturonan (AP), rhamnogalacturonan I (RG-I) and rhamnogalacturonan II (RG-II). HG is the most abundant and the simplest pectin since it is a linear galacturonic acid chain, which is partially methylesterified and acetylated. XGA is a HG substituted with xylose and AP is a HG substituted with D-apiofuranose. RG-II is the most structurally complex pectin. (Mohnen, 2008) It consists of a HG backbone with side chains consisting of 12 different sugars in over 20 different linkages. The sugars are D-glucuronic acid, L-rhamnose, D-galactose, L-arabinose, L-fucose, D-apiose, L-aceric acid, 2-O-methyl L-fucose, 2-O-methyl D-xylose, L-galactose, 2-keto-3-deoxy-D-lyxo-heptulosaric acid and 2-keto-3-deoxy-D-manno-octulosonic acid. (O'Neill et aL, 2004) In contrast to other pectin types, the RG-I backbone consists of a α-1,4-linked D-galacturonic acid and α-1,2-linked L-rhamnose repeating disaccharide unit with side chains consisting of various amount of L-arabinose and D-galactose. (Mohnen, 2008)

The main constituent of pectin, D-galacturonic acid, can be catabolized by some microorganisms. For example, the filamentous fungus, e.g. *A. niger*, is naturally capable of hydrolyzing pectin and catabolizing D-galacturonic acid to pyruvate and glycerol. In this reductive pathway, D-galacturonate (salt of galacturonic acid) is first reduced to L-galactonate by D-galacturonate reductase and then L-galactonate dehydratase removes a water molecule generating 3-deoxy-L-threo-hex-2-ulosonate. Next 2-keto-3-deoxy-L-galactonate aldolase splits 3-deoxy-L-threo-hex-2-ulosonate to pyruvate and L-glyceraldehyde. Finally, L-glyceraldehyde is reduced to glycerol by glyceraldehyde reductase. (Richard and Hilditch, 2009)

Figure 1:
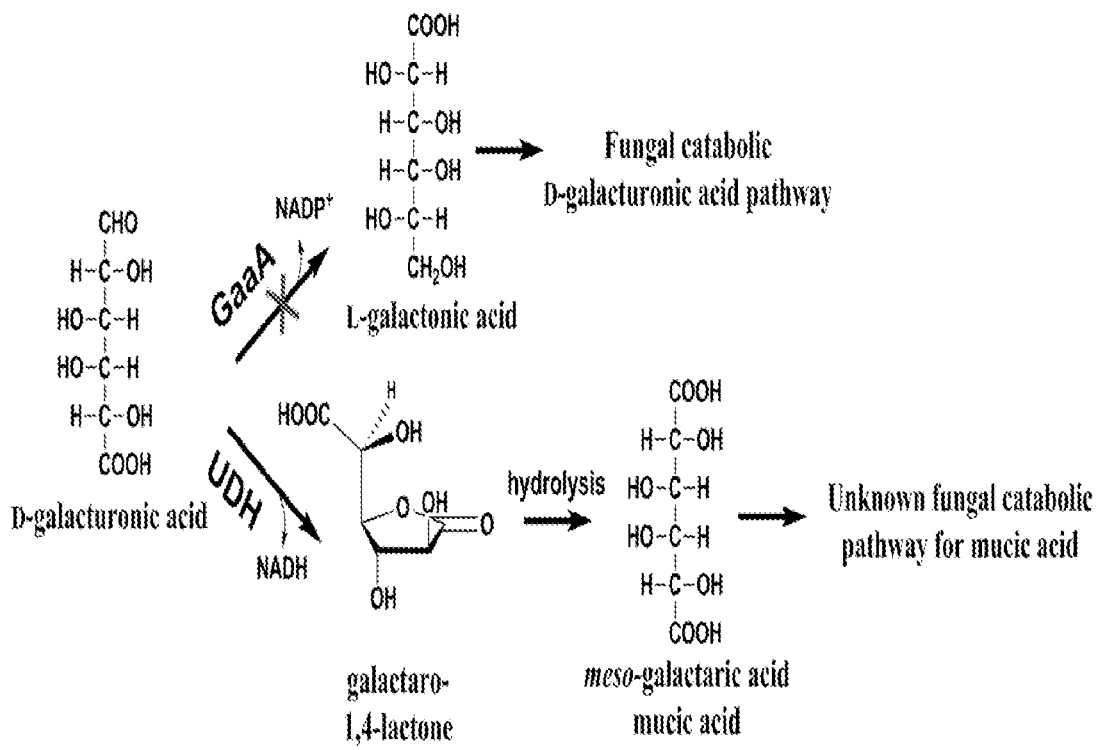
FIG. 1 shows the first enzyme, GaaA, in the fungal catabolic D-galacturonic acid pathway in *A. niger* and a heterologous uronate dehydrogenase (UDH) for meso-galactaric acid production.

Meso-galactaric acid can be produced by the oxidation of D-galacturonic acid—the main constituent in pectin. In the biochemical oxidation route, a bacterial enzyme—uronate dehydrogenase—may be heterologously expressed in fungal and bacterial hosts resulting in production of meso-galactaric acid from D-galacturonic acid (FIG. 1).

A nucleotide sequence encoding uronate dehydrogenase enzyme (EC 1.1.1.203) suitable for the present invention can be isolated from any organism producing this enzyme comprising eukaryotes and including animals (and man), plants, fungi, yeasts or prokaryotes including bacteria. Specifically a nucleotide sequence encoding uronate dehydrogenase enzyme of the present invention is isolated from a microbial source, such as from bacteria or fungi, in particular from bacteria. According to a specific embodiment of the invention a nucleotide sequence encoding uronate dehydrogenase enzyme of the present invention is obtainable from genus *Agrobacterium*, more specifically from *A. tumefaciens*. According to a another embodiment of the invention a nucleotide sequence encoding the enzyme is obtainable from a commercial culture collection strain, e.g. C 58, ATCC, American Type Culture Collection. According to a specific embodiment of the invention a nucleotide sequence encoding uronate dehydrogenase enzyme is obtainable from genus *Pseudomonas*. According to a very specific embodiment of the invention a nucleotide sequence encoding the enzyme is available in the GenBank, e.g. as GenBank accession number EU377538. In a further embodiment of the invention the uronate dehydrogenase enzyme is a heterologous (e.g. bacterial) uronate dehydrogenase enzyme, e.g. originating from *Pseudomonas* or *Agrobacterium* genera. In a specific embodiment uronate dehydrogenase enzyme is D-galacturonate dehydrogenase enzyme.

The origin of a polynucleotide sequence encoding uronate dehydrogenase enzyme of the present invention is not restricted to any specific genus or species. A person skilled in the art can find or isolate a polynucleotide sequence encoding uronate dehydrogenase enzyme of the present invention from other genera of bacteria or fungi or from other organisms.

Polynucleotide sequences encoding uronate dehydrogenase enzyme in various organisms can be isolated and the amino acid sequences encoded by the nucleotide sequences can be compared with the amino acid sequence of the uronate dehydrogenase enzyme isolated and characterized e.g. in WO2010/072902 A1. Homologues of uronate dehydrogenase enzymes can be identified by any conventional methods known in the art, for example by carrying out a BLAST or FASTA search.

A person skilled in the art can also identify a conserved region in the nucleotide or amino acid sequence and clone a gene fragment using PCR techniques. After sequencing the fragment the complete gene can be obtained for example by using cDNA library in a vector as described by Richard et al. (2001). A nucleotide sequence encoding uronate dehydrogenase enzyme can be identified also by nucleic acid hybridization.

Standard molecular biology methods can be used in the cloning of the uronate dehydrogenase enzyme i.e. in the isolation and enzyme treatments of DNA, in *E. coli* transformations, the isolation of a fragment comprising the uronate dehydrogenase gene by amplification in a PCR reaction (Coen D M, 2001) and in the techniques for codon change. The basic methods used are described in the standard molecular biology handbooks, e.g. Sambrook et al. (1989) and Sambrook and Russell (2001). Insertion of the nucleotide sequence under a strong promoter in an expression vector, transfer of the vector into suitable host cells and cultivation of the host cells in conditions provoking production of said enzyme. Methods for protein production by recombinant technology in different host systems are well known in the art (Gellissen, 2005). Cloning and expression of the D-galacturonic acid dehydrogenase in a heterologous host has also been well described e.g. in publications Mojzita et al. (2010) and WO2010/072902 (A1). These methods are suitable also for the present invention.

As used herein "a recombinant fungal cell" refers to any fungal cell that has been genetically modified to contain different genetic material compared to the fungal cell before modification. "The recombinant fungal cell" of the invention also refers to a host cell, which comprises a vector or plasmid comprising at least a polynucleotide encoding uronate dehydrogenase.

A recombinant micro-organism that has been "genetically modified to express" or "genetically modified to overexpress" includes embodiments, where a polynucleotide encoding a polypeptide has been transformed into a cell in such a manner that the cell is capable of producing an active polypeptide. As used herein, "expression" or "overexpression" achieved by a genetic modification of a fungal cell refers to excessive expression of a polynucleotide by producing more products (e.g. polypeptide) than an unmodified fungal cell. One or more copies of a polynucleotide may be transformed to a cell for expression or overexpression. The term also encompasses embodiments, where a promoter region has been modified to allow or to increase the expression of a polynucleotide in a fungal cell.

Activity and/or lack of activity of an uronate dehydrogenase enzyme can be confirmed by using known assay methods. E.g. Chang and Feingold (1969) and references therein have described the enzyme activity of uronate dehydrogenase.

An engineered fungal cell of the present invention comprises a genetic or non-genetic modification reducing D-galacturonic acid reductase (EC.1.1.1.19) activity. As used herein "reduced D-galacturonic acid reductase activity" refers to the presence of less D-galacturonic acid reductase activity, if any, compared to a wild type D-galacturonic acid reductase polypeptide, or lower D-galacturonic acid reductase activity (if any) in a cell compared to a cell comprising wild type D-galacturonic acid reductase. Reduced D-galacturonic acid reductase activity may result e.g. from down regulation of the polynucleotide or polypeptide expression, deletion of at least part of the D-galacturonic acid reductase polynucleotide or polypeptide, and/or lowered activity of D-galacturonic acid reductase polypeptide. An example of non-genetic methods includes but is not limited to a use of inhibitors (i.e. molecules that bind to a polynucleotide, a polypeptide or enzyme thereby decreasing its activity) of D-galacturonic acid reductases.

The fungal cell of the invention may comprise one or several genetic D-galacturonic acid reductase modifications. A genetic modification lowering D-galacturonic acid reductase activity may refer to a deletion or substitution of one or more nucleic acids or any fragment of a polynucleotide sequence encoding D-galacturonic acid reductase or any insertion of one or more nucleic acids or any nucleic acid sequence fragment into said polynucleotide sequence. Reduced activity of D-galacturonic acid reductase may be tested for example by a growth experiment, wherein a genetically modified fungal strain is grown on a medium in the presence of 2% D-galacturonic acid as a sole carbon source e.g. described in WO2010/072902 A1. As an example a mutant strain having no D-galacturonic acid reductase activity is not able to grow under these conditions.

In some embodiments, the genetic modification down regulates the expression of D-galacturonic acid reductase polynucleotide or polypeptide. As used herein "down regulated expression" refers to decreased expression, including lack of expression, of the gene or polypeptide of interest compared to a wild type fungal cell without the genetic modification. Lack of expression or decreased expression can be proved for example by western, northern or southern blotting or quantitative PCR or any other suitable method known to a person skilled in the art. Genetic modification leading to down-regulation of a polynucleotide or polypeptide refers to a deletion of D-galacturonic acid reductase polynucleotide, or one or more nucleotides or a fragment thereof, or one or more nucleotides or a fragment of a regulatory sequence (i.e. a sequence that regulates the expression of a polynucleotide (e.g. promoter area) or polypeptide) decreasing the expression of a polynucleotide or polypeptide. Also, any nucleotide insertions or substitutions (one or more nucleotides including long nucleotide sequences) in a polynucleotide or in a regulatory sequence of this polynucleotide may have an effect of decreasing the expression of a polynucleotide or polypeptide and thus, may be utilized in the present invention. Also, epigenetic modifications such as DNA methylation are known to block expression of genes and can be utilized in the present invention. Furthermore, e.g. RNA interference is also known to down-regulate translation of polypeptides. In certain embodiments, the genetic modification includes temporary or permanent silencing of D-galacturonic acid reductase gene.

The knowledge of the DNA sequence of D-galacturonic acid reductase can be used to inactivate the corresponding polynucleotide in a suitable fungal cell. The polynucleotide can be inactivated e.g. by preventing its expression or by mutation or deletion of the polynucleotide or part thereof. There are various techniques for inactivating a gene. These techniques make use of the nucleotide sequence of the gene or of the polynucleotide sequence in the proximity of the gene. In a specific embodiment the recombinant fungal cell has been genetically modified by deleting a polynucleotide encoding the D-galacturonic acid reductase or part thereof. For example gene knockout methods are suitable for disrupting a natural pathway for utilization of D-galacturonic acid, namely deleting the nucleotide sequence that encodes a polypeptide having D-galacturonic acid reductase activity, or any part thereof. These methods have been described for example in publications Mojzita et al. (2010) and WO2010/072902 A1, they are well-known to a person skilled in the art and they can be used for the present invention.

Examples of D-galacturonic acid reductase are not limited to gar1 or gar2 in *H. jecorina* and the gaaA in *Aspergillus niger*. Indeed, as used herein "D-galacturonic acid reductase" refers to any fungal polypeptide having D-galacturonic acid reductase acivity.

A "fragment" or "part" of a given sequence means any part of that sequence, for example one or several nucleotides or amino acids or a truncated form of the sequence.

As used herein, "a polynucleotide" refers to any polynucleotide, such as single or double-stranded DNA (genomic DNA or cDNA) or RNA, comprising a nucleic acid sequence encoding a specific polypeptide or a conservative sequence variant thereof.

Herein, the term "polypeptide" refer to polymers of amino acids of any length. As used herein "enzyme" refers to a polypeptide or group of polypeptides having activity as a catalyst. Enzymes accelerate, or catalyze, chemical reactions.

In connection with polynucleotides, the term "conservative sequence variant" refers to nucleotide sequence modifications, which do not significantly alter biological properties of the encoded polypeptide. Conservative nucleotide sequence variants include variants arising from the degeneration of the genetic code and from silent mutations. Nucleotide substitutions, deletions and additions are also contemplated.

Identity of any sequence or fragments thereof compared to the sequence of this disclosure refers to the identity of any sequence compared to the entire sequence of the present invention. As used herein, the % identity between the two sequences is a function of the number of identical positions shared by the sequences (i.e. % identity=# of identical positions/total # of positions×100), taking into account the number of gaps, and the length of each gap, which need to be introduced for optimal alignment of the two sequences. The comparison of sequences and determination of identity percentage between two sequences can be accomplished using mathematical algorithms available in the art. This applies to both amino acid and nucleic acid sequences.

Sequence identity may be determined for example by using BLAST (Basic Local Alignment Search Tools) or FASTA (FAST-All). In the searches, setting parameters "gap penalties" and "matrix" are typically selected as default.

Polypeptides or polynucleotides "from", "derived from", "originated from" or "obtained from" a particular organism encompass products isolated from said organism, as well as modifications thereof. A protein derived from a particular organism may be a recombinantly produced product, which is identical to, or a modification of the naturally occurring protein. The protein may also be modified e.g. by glycosylation, phosphorylation or other chemical modification. Products derived from the particular organism also encompass mutants and natural variants of the products, where one or more nucleic acid and/or amino acid is deleted, inserted and/or substituted.

By "homologous" is meant something originating from the same species as the host. By "heterologous" is meant something from another species as the host or from other genera as the host. If the host organism is a fungus, the heterologous nucleotide sequence may mean a nucleotide sequence from a prokaryote, such as from bacteria.

Fungal cells efficient in pectin hydrolysis are also capable of catabolizing the resulting meso-galactaric acid via unknown catabolic pathway. This catabolic pathway has not been described before. In this study, transcriptomics approach was used to identify genes involved in meso-galactaric acid catabolism in fungal cells. Catabolism of meso-galactaric acid was disrupted in a fungal cell by deleting a polynucleotide of said catabolic pathway (see Tables 1 and 2, Protein IDs are based on Joint Genome institute (JGI), JGI *Aspergillus niger* ATCC 1015 v4.0 genomic database). Altogether seven different genes of said catabolic pathway were deleted in the experiments.

Meso-galactaric acid catabolism may be reduced by genetic or non-genetic methods. An example of non-genetic methods includes but is not limited to a use of inhibitors (i.e. molecules that bind to a polynucleotide, a polypeptide or enzyme thereby decreasing its activity) of a polynucleotide, a polypeptide or polypeptides of the meso-galactaric acid pathway. Genetic modifications reducing D-galacturonic acid reductase activity described earlier in the present disclosure apply also to genetic modifications of polynucleotides of meso-galactaric acid catabolic pathway.

In one embodiment of the invention meso-galactaric acid catabolism has been decreased by deleting at least part of one or more polynucleotides encoding polypeptides participating in meso-galactaric acid catabolism or by decreasing expression or activity of one or more polypeptides participating in meso-galactaric acid catabolism. An engineered fungal strain combining the disrupted meso-galactaric acid catabolism, disrupted D-galacturonic acid catabolism and expression of a heterologous UDH produced meso-galactaric acid from D-galacturonic acid with an excellent yield. In addition, the strain was capable of consolidated bioprocess from pectin-rich biomass to meso-galactaric acid.

In one embodiment of the invention any polynucleotide of the meso-galactaric acid catabolic pathway, e.g. any one of those mentioned in Table 1 or 2, may be deleted according to the present invention. Alternatively, expression of the polynucleotides mentioned in Table 1 or 2 may be decreased or activity of one or more corresponding polypeptides may be reduced. Furthermore, anyone of the primers or probes mentioned in Table 1 or 2 may be used for identifying the polypeptide to be genetically modified.

As used herein, "catabolic pathway" refers to a pathway that breaks down molecules into smaller units that are either oxidized to release energy, or used in other reactions. Therefore, in this context a pathway is a series of chemical reactions occurring within a cell. The meso-galactaric acid catabolic pathway is a pathway breaking down meso-galactaric acids.

In some embodiments, the nucleic acid sequence to be genetically modified may comprise a polynucleotide sequence encoding a polypeptide having JGI ID number selected from the group consisting of 39114 (SEQ ID NO: 72), 1090836 (SEQ ID NO: 73), 1117792, 1141260, 1121140 (SEQ ID NO: 74), 1146483 and 1170646; or the nucleic acid sequence to be genetically modified may comprise a polynucleotide sequence having at least 80%, 85%, 90%, 95%, 96%, 97%, 98%, 99% or 100% nucleic acid sequence identity with a polynucleotide sequence encoding a polypeptide having JGI ID number selected from the group consisting of 39114, 1090836, 1117792, 1141260, 1121140, 1146483 and 1170646, and encoding a polypeptide of the meso-galactaric acid catabolic pathway.

The polypeptide 39114 has a predicted function of α-aminoadipate-semialdehyde dehydrogenase (EC 1.2.1.31) also known as α-aminoadipate reductase (AAR) (Napora-Wijata et al., 2014). The polypeptides 1090836 and 1121140 were predicted to be members of the protein families aldo/keto reductases and FAD-dependent oxidoreductases, respectively. The polypeptides 1117792, 1141260, 1146483 and 1170646 were predicted to be members of the protein families alcohol dehydrogenases, short-chain dehydrogenases/reductases, mandelate racemase/muconate lactonizing enzymes and D-isomer specific 2-hydroxyacid dehydrogenases respectively. Enzymatic activities of these proteins also remain unknown.

In a very specific embodiment the polypeptide (s) of the meso-galactaric acid catabolic pathway is (are) selected from the group consisting of AMP-dependent synthetase and ligase, α-aminoadipate-semialdehyde dehydrogenase, aldo/keto reductase, zinc-binding alcohol dehydrogenase, short-chain dehydrogenase/reductase, FAD-dependent oxidoreductase, mandelate racemase/muconate lactonizing enzyme and D-isomer specific 2-hydroxyacid dehydrogenase, and any combination thereof.

In some embodiments of the invention the slow transport of D-galacturonic acid into the cell might slow down the conversion of D-galacturonic acid to meso-galactaric acid. In this case the expression of genes coding for D-galacturonic acid transport molecules can facilitate the conversion of uronic acids. For example, if the host is yeast, such as S. cerevisiae, the introduction of a transporter to facilitate the transport of D-galacturonic acid into the fungal cell may be recommended. Expression of a transporter gene for D-galacturonic acid has been well described in publication WO2010/072902 (A1) and said methods and transporter genes are also suitable for the present invention.

In a specific embodiment in addition to any other modifications (e.g. UDH expression, deletion of at least part of a polynucleotide encoding D-galacturonic acid reductase and reduced meso-galactaric acid catabolism) the fungal cell has further been genetically modified by deleting at least part of a polynucleotide encoding 2-keto-3-deoxy-L-galactonate aldolase.

In one embodiment of the invention the recombinant fungal cell further comprises other genetic modifications than described above in the disclosure. "Other genetic modifications" include any genetic modifications e.g. addition of plasmids, insertions, substitutions, deletions or disruptions of one or more polynucleotides or parts thereof, e.g. one or more nucleotides. Also epigenetic modifications such as methylation are included in "other genetic modifications". Furthermore, the cell may be genetically modified to produce or not to produce other compounds than meso-galactaric acid. Methods for any genetic modifications are generally well known and are described in various practical manuals describing laboratory molecular techniques.

The genetically modified fungal cells used in the invention are obtained by performing specific genetic modifications to a fungal cell. As used herein, a "recombinant fungal cell" refers to any fungal cell that has been genetically modified to contain different genetic material compared to the micro-organism before modification (e.g. comprise a deletion, substitution, disruption or insertion of one or more nucleic acids compared to the fungal cell before modification). The fungal cell of the invention is genetically modified to produce meso-galactaric acid. At least three different polynucleotides or any regulatory nucleotide sequence of a gene are modified according to the present invention.

"Fungi" "fungus" and "fungal" as used herein refer to any yeast and filamentous fungi i.e. moulds. A genetically modified fungal cell may also be referred to as a host cell. A fungal cell selected for the present invention is suitable for genetic manipulation and often can be cultured at cell densities useful for industrial production of a target product. A fungal cell selected may be maintained in a fermentation device. In one embodiment of the invention the fungal cell is a uracil auxotrophic cell. In another embodiment the fungal cell is naturally capable of degrading pectin. In a specific embodiment of the invention the fungal cell produces sufficiently pectinolytic enzymes to hydrolyse pectin and pectinolytic enzymes do not have to be supplemented.

In a specific embodiment the fungal cell is a mould or filamentous fungi. In another embodiment the fungal cell is selected from the genera *Aspergillus*, *Hypocrea* or *Trichoderma*. In another very specific embodiment the fungal cell is selected from the group consisting of *Aspergillus niger, A. oryzae, A. terreus, A. nidulans, A. kawachii* and *A. fischeri* and *Trichoderma reesei*. E.g. *Aspergillus* fungal cells are excellent organisms for the present invention because they produce efficiently pectinases that are hydrolysing pectin to the galacturonic acid which is the substrate of the process.

The genetically modified fungal strain of the present invention was the engineered to convert galacturonate to galactarate, but is not able to catabolize galactarate.

According to an embodiment of the invention, in the method of converting galacturonic acid to meso-galactaric acid, a fungal cell is contacted with a biomaterial comprising galacturonic acid or pectin in order to convert at least a portion of the galacturonic acid to meso-galactaric acid.

Thus, according to this embodiment, biomass comprising a sugar acid or a derivative thereof is fermented by a microorganism capable of converting D-galacturonic acid to meso-galactaric acid and optionally the desired compounds produced are recovered.

In one embodiment, the present invention is directed to a method, which comprises cultivating a genetically modified fungal cell under conditions allowing expression of the UDH.

In the method of the invention, a recombinant fungal cell is cultured in a growth and production medium that includes compounds for growth and energy. The medium used for producing meso-galactaric acid is any conventional medium, such as aqueous media, or solid media for culturing the fungal cell of the invention. For example, suitable media include but are not limited to the following: natural media composed of natural substrates, such as herbaceous or woody stems, seeds, leaves, corn meal, wheat germ, and oatmeal etc.; corn meal agar; potato dextrose agar; V-8 juice agar; dung agar; synthetic media; Czapek-Dox medium; glucose-asparagine and Neurospora crassa minimal medium; Yeast Extract Peptone (YP) media, Yeast Extract Peptone Dextrose (YPD) media, or any medium suitable for culturing filamentous fungi or yeast.

The carbon substrate used as a source for meso-galactaric acid production may be provided as pure substrates or from complex sources. Carbon substrate can be any carbon substrate, which can be directly or through one or more steps converted to D-galacturonic acid. In a specific embodiment of the invention, the carbon substrate is pectin or any source comprising pectin or rich in pectin (such as non-woody plant biomass e.g. fruit peels, citrus fruit and sugar beet). The medium may also contain alternative carbon sources, such as ethanol, glycerol, acetate, L-arabinose, D-galacturonate or amino acids.

In addition, the medium may consist of or contain complex, poorly defined elements, such as corn steep liquor or solids, or molasses. Sugars of the fermentation medium are also present. In case of oligomeric sugars, it may be necessary to add enzymes to the fermentation broth in order to digest these to the corresponding monomeric sugar. The medium will typically contain nutrients required by the particular micro-organism, including a source of nitrogen (such as amino acids, proteins, inorganic nitrogen sources such as ammonia or ammonium salts), and various vitamins and minerals. Also any other agents or compounds may be present in the medium according to the common general knowledge of the art.

Other fermentation conditions, such as temperature, cell density, selection of nutrients, and the like are not considered to be critical to the invention and are generally selected to provide an economical process. Such conditions are within the knowledge of a skilled person and can be selected depending on the fungal cell in question.

Temperatures during each of the growth phase or the production phase may range from above the freezing temperature of the medium to about 50° C., although the optimal temperature will depend somewhat on the particular micro-organism. In one embodiment a temperature is from about 15 to 37° C.

The pH of the process may or may not be controlled to remain at a constant pH, but may specifically be between about 3.0 and 8.0, depending on the production organism. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

The fermentation is conducted aerobically or microaerobically. If desired, a specific oxygen uptake rate can be used as a process control. The process of the invention can be conducted continuously, batch-wise, or any combination thereof.

According to one embodiment of the present invention a fungal cell is cultured under suitable culture conditions for producing increased levels of meso-galactaric acid. The increase may be at least a 2, 3, 5, 10, 15, 20, 50 or 100 fold increase in meso-galactaric acid concentration compared to the unmodified strain or any strain with other modifications during cultivation. Alternatively, it may be at least a 2, 3, 5, 10, 15, 20, 50 or 100 fold increase in meso-galactaric acid yield per used carbon source in transformants compared to the unmodified strain or any strain with other modifications. It may also refer to at least a 2, 3, 5, 10, 15, 20, 50 or 100 fold increase in meso-galactaric acid production rate (g/l) compared to the unmodified strain or any strain with other modifications. In a very specific embodiment the meso-galactaric acid production reaches values 1 g/l, 2 g/l, 3 g/l, or 4 g/l. The increase of meso-galactaric acid production can be detected either intracellularly or in culture medium.

After culturing fungal cells the meso-galactaric acid can be recovered by disrupting the cells and/or directly from the culture medium without disrupting the cells. In one embodiment of the invention the method of producing meso-galactaric acid further comprises an optional step d) of isolating and purifying the meso-galactaric acid from the medium. Meso-galactaric acid may be isolated and purified from the medium by using any conventional methods known in the art such as ion exchange, two phase extraction, molecular distillation, melt crystallization, hexane extraction, $CO_2$ extraction or distillation.

The meso-galactaric acid obtained by the method of the present invention can be used for preparing e.g. polymers. As an example, meso-galactaric acid may be chemically reduced to adipic acid and/or 2,5-furandicarboxylic acid (FDCA), precursors of polymers.

The present invention also relates to a method for identifying a polynucleotide or polypeptide of the meso-galactaric acid catabolic pathway, wherein the method comprises contacting a wild type fungal cell with meso-galactaric acid, carrying out a transcriptional analysis on a sample obtained from the wild type fungal cell contacted with meso-galactaric acid, and identifying overexpressed polynucleotides compared to a sample obtained from a wild type fungal cell not contacted with meso-galactaric acid. As used herein "wild type" refers to a fungal cell, which has not been genetically modified.

A transcriptional analysis may be carried out by any methods known to a person skilled in the art. Gene expression profiling is the measurement of the activity (the expression) of thousands of genes at once, to create a global picture of cellular function. These profiles can, for example, distinguish between cells that are actively dividing, or show how the cells react to a particular treatment. Many experiments of this sort measure an entire genome simultaneously, that is, every gene present in a particular cell. However, an entire genome does not need to be studied simultaneously.

A transcriptional analysis methods include but are not limited to hybridization-based microarrays, utilization of Expressed Sequence Tag libraries or chemical tag-based methods (e.g., serial analysis of gene expression), DNA microarray technology and RNA Sequencing.

DNA microarray technology measures the relative activity of previously identified target genes. Sequence based techniques, like serial analysis of gene expression (SAGE, SuperSAGE) are also used for gene expression profiling. SuperSAGE is especially accurate and can measure any active gene, not just a predefined set. The advent of next-generation sequencing has made sequence based expression analysis an increasingly popular, "digital" alternative to microarrays called RNA-Seq. RNA-seq (RNA sequencing, or also called whole transcriptome shotgun sequencing) uses next-generation sequencing to reveal the presence and quantity of RNA in a biological sample at a given moment in time. RNA-Seq is used to analyze the continually changing cellular transcriptome, specifically e.g. alternative gene spliced transcripts, post-transcriptional modifications, gene fusion, mutations/SNPs and changes in gene expression, and different populations of RNA to include mRNA, total RNA, small RNA, such as miRNA, tRNA, and ribosomal profiling.

In a specific embodiment of the invention total RNA was extracted from the fungal cell contacted with meso-galactaric acid for RNA sequencing, and optionally also from a fungal cell not contacted with meso-galactaric acid, for transcriptional analysis e.g. RNA sequencing.

In a specific embodiment the overexpressed polynucleotides were further analysed with enzyme prediction for potential carbohydrate metabolism. Such prediction programs are well known to a person skilled in the art and commercially available.

In one embodiment of the invention the method for identifying a polynucleotide or polypeptide of the meso-galactaric acid catabolic pathway further comprises: deleting a polynucleotide, which was identified as overexpressed or further analyzed as a potential polynucleotide or polypeptide of the meso-galactaric acid catabolic pathway according to said method, or part thereof from a fungal cell, and optionally identifying whether the fungal cell is capable of producing meso-galactaric acids. Methods suitable for decreasing meso-galactaric acid catabolism or deleting polynucleotides have been described above in the disclosure.

In a specific embodiment the method for identifying a polynucleotide or polypeptide of the meso-galactaric acid catabolic pathway further comprises genetic modification of a fungal cell capable of converting D-galacturonic acid to meso-galactaric acid by expressing uronate dehydrogenase enzyme, by reducing (e.g. by deleting at least part of a polynucleotide encoding D-galacturonic acid reductase) D-galacturonic acid reductase activity, and by reducing meso-galactaric acid catabolism. A cell to be modified may be the cell identified to have overexpressed polynucleotides or polypeptides, or any other cell (e.g. from different genera or species). Genetic modifications suitable for said fungal cell have been described above in the disclosure. In a more specific embodiment a putative gene was deleted using CRISPR/Cas9 technology, optionally together with in vitro synthesized single chimeric guide RNA (sgRNA), and as a result meso-galactaric acid catabolism was disrupted in the fungal cell. In a very specific embodiment of the invention any primer or primers of Table 1 may be utilized in the present invention.

Indeed, polynucleotide targeting (i.e. gene targeting) may be utilized in any genetic modifications of the present invention for deleting or replacing nucleotide sequences. Polynucleotide targeting uses homologous recombination to target desired changes to a specific endogenous polypeptide. Polynucleotide targeting may be carried out by any methods or techniques well known in the art. Methods for genetic targeting are described in various practical manuals describing laboratory molecular techniques. A person skilled in the art knows when and how to employ these methods. The success of polynucleotide targeting can be enhanced with the use of engineered nucleases. The nucleases create specific double-stranded break at desired locations in the genome, and harness the cell's endogenous mechanisms to repair the induced break by natural processes of homologous recombination and nonhomologous end-joining. Nucleases suitable for the present invention include but are not limited to, zinc finger nucleases, engineered homing endonucleases, transcription activator-like effector nucleases (TALENs), the CRISPR/Cas system and engineered meganucleases.

In the present invention polynucleotide targeting may be used to insert polynucleotides into or delete polynucleotides from target polynucleotides. Polynucleotide targeting can be permanent or conditional. Polynucleotide targeting requires the creation of a specific vector for each target polynucleotide of interest. The term "vector" refers to a nucleic acid compound and/or composition that transduces a cell, thereby causing the cell to express polynucleotides and/or polypeptides other than those native to the cell, or in a manner not native to the cell.

It will be obvious to a person skilled in the art that, as the technology advances, the inventive concept can be implemented in various ways. The invention and its embodiments are not limited to the examples described above but may vary within the scope of the claims.

EXAMPLES

1. Materials and Methods
1.1. Strains

The *Aspergillus niger* strain ATCC 1015 (CBS 113.46) was used as a wild type. The *A. niger* ΔpyrG strain (deleted orotidine-5'-phosphate decarboxylase) and the platform strain for meso-galactaric acid production ΔgaaA-udh (deleted D-galacturonate reductase and introduced uronate dehydrogenase) were described previously (Mojzita et al., 2010; WO2010/072902 (A1)). All the plasmids were produced in *Escherichia coli* TOP10 cells. The *Saccharomyces cerevisiae* strain ATCC 90845 was used in the homologous recombination for the construction of deletion cassettes.

1.2. Media and Culture Conditions

Luria Broth culture medium supplemented with 100 μm $ml^{-1}$ of ampicillin and cultural conditions of 37° C. and 250 rpm were used for *E. coli* cultures. YP-medium (10 g yeast extract $1^{-1}$, and 20 g peptone $1^{-1}$) supplemented with 20 g D-glucose $1^{-1}$ was used for yeast pre-cultures. After the transformations in yeast, SCD-URA (uracil deficient synthetic complete media supplemented with 20 g D-glucose $1^{-1}$) plates were used for uracil auxotrophic selection. All the yeast cultivations were carried out at 30° C. and the liquid cultivations at 250 rpm. *A. niger* spores were generated on potato-dextrose plates and ~$10^8$ spores were inoculated to 50 ml of YP medium (10 g yeast extract $1^{-1}$, 20 g peptone $1^{-1}$) containing 30 g gelatin $1^{-1}$ for pre-cultivations. Mycelia were pre-grown in 250-ml Erlenmeyer flasks by incubating overnight at 28° C., 200 rpm and harvested by vacuum filtration, rinsed with sterile water and weighted. In *A. niger* transformations, *A. nidulans* defined minimal medium (Barratt et al., 1965) plates supplemented with 1.2 M D-sorbitol and 20 g agar $1^{-1}$ and, in the case of CRISPR/Cas9 transformations, 400 μm/ml hygromycin were used. The minimal medium used in the phenotypic characterization in liquid cultivations contained 10 g meso-galactaric acid $1^{-1}$ with or without 0.5 g D-xylose $1^{-1}$ and the pH was adjusted to 7.0. These cultivations were inoculated with 10 g $1^{-1}$ (wet) of pre-grown mycelia. Alternatively, YP-medium supplemented with 10 g meso-galactaric acid $1^{-1}$ was used. Similar minimal or YP-medium supplemented with 20 g D-galacturonic acid $1^{-1}$ pH 5 was used in the cultivations for meso-galactaric acid production and were inoculated with 10 gl$^{-1}$ (wet) of pre-grown mycelia. For the consolidated process, the minimal medium was supplemented with 40 g l$^{-1}$ of orange processing waste as described earlier (Kuivanen et al., 2015).

1.3. Transcriptional Analysis

*A. niger* wild type strain was cultivated in the minimal medium supplemented with meso-galactaric acid. Samples of 2 ml were collected and the mycelium was harvested by vacuum filtration. The filtered mycelium was frozen with liquid nitrogen and stored at −80° C. Total RNA was extracted using the RNeasy Plant Mini Kit (Qiagen). RNA library preparation and sequencing was carried out by GATC (Constance, Germany) using the InView™ Transcriptome Explore package. The raw data was processed as described earlier (Kuivanen et al. 2016).

1.4. Gene Deletions

For the deletion of the genes identified in the RNA sequencing, deletion cassettes containing homologous 5' and 3' flanks (~1.5 kb) for targeted integration and the selectable marker pyrG (*A. niger*) were constructed. The 5' and 3' flanks were amplified by PCR (KAPA HiFi DNA polymerase, Kapa Biosystems) with the primers described in table 1. The amplified flanks and pyrG were joined using yeast homologous recombination, produced in *E. coli* and the resulting cassettes were linearized with NotI (Thermo). The linearized cassettes (10 μm) were transformed to *A. niger* ΔpyrG strain with or without the pFC-332 plasmid expressing Cas9 (1 jig) (Nodvig et al., 2015) and two suitable in vitro synthesized sgRNAs (10 jig) (GeneArt™ Precision Synthesis Kit) as described in table 1. In the generation of meso-galactaric acid producing strain, the genes with the ID 39114, 1090836 and 1121140 were deleted from the strain ΔgaaA-udh. All the *A. niger* transformations were carried out using the protoplast transformation method. Correct integration of the transformed cassette into the genome was confirmed with colony PCR using Phire direct PCR kit (Thermo Scientific) and the primers listed in table 1.

TABLE 1

Primers for the construction of gene deletion cassette, primers for colony PCR and sgRNA sequences.

Primers for the construction of gene deletion cassette

| Name | Sequence | Description |
| --- | --- | --- |
| oPEEL-007 | CCCCCCCTCGAGGTCGACGGTATCGAT AAGCTTGATATCGGCGGCCGCCACGCG TTTCCACATCTTCT (SEQ ID NO: 1) | For the deletion cassette of ID1146483 (dgdB), 5'flank for, flank for EcoRI/BamHI digested B2974 |
| oPEEL-008 | CTGGTATAGCCAAACATCGCCAATCAC CTCAATCACCCGGATTAGCAATGTGCT GCTTGC (SEQ ID NO: 2) | For the deletion cassette of ID1146483 (dgdB), 5'flank rev, flank for XmaI digested pyrG |
| oPEEL-009 | GCCATGCGGGCTTGGGACGCCATGTCC GTCGCGTGATAACGTGATTGCGGAGG TGATCTG (SEQ ID NO: 3) | For the deletion cassette of ID1146483 (dgdB), 3'flank for, flank for XmaI digested pyrG |
| oPEEL-010 | AGCTCCACCGCGGTGGCGGCCGCTCTA GAACTAGTGGATCGCGGCCGCGAAACT GATCGATCAGTCAC (SEQ ID NO: 4) | For the deletion cassette of ID1146483 (dgdB), 3'flank rev, flank for EcoRI/BamHI digested B2974 |
| oPEEL-017 | CCCCCCCTCGAGGTCGACGGTATCGAT AAGCTTGATATCGGCGGCCGCGACAGG GTTGAGCCAGTCTA (SEQ ID NO: 5) | 5' flank aplification for An ID 1090836 del cassette, For, flank for EcoRI/BamHI dig pPEEL-001 |
| oPEEL-018 | CTGGTATAGCCAAACATCGCCAATCAC CTCAATCACCCGGTGCGACTAGTTGGG TGTCAC (SEQ ID NO: 6) | 5' flank aplification for An ID 1090836 del cassette, Rev, flank for pyrG (pPEEL-002) |
| oPEEL-019 | GCCATGCGGGCTTGGGACGCCATGTCC GTCGCGTGATAACCAGGATTGTACAA CTTAGTT (SEQ ID NO: 7) | 3' flank aplification for An ID 1090836 del cassette, For, flank for pyrG (pPEEL-002) |
| oPEEL-020 | AGCTCCACCGCGGTGGCGGCCGCTCTA GAACTAGTGGATCGCGGCCGCGTACAT CTCAGGGTAATATC (SEQ ID NO: 8) | 3' flank aplification for An ID 1090836 del cassette, Rev, flank for EcoRI/BamHI dig pPEEL-001 |
| oPEEL-024 | CCCCCCCTCGAGGTCGACGGTATCGAT AAGCTTGATATCGGCGGCCGCCTACGA GCCGTAGATTGCGT (SEQ ID NO: 9) | 5' flank aplification for An ID 1117792 del cassette, For, flank for EcoRI/BamHI dig pPEEL-001 |

TABLE 1-continued

Primers for the construction of gene deletion cassette, primers for colony PCR and sgRNA sequences.

| | | |
|---|---|---|
| oPEEL-025 | CTGGTATAGCCAAACATCGCCAATCAC CTCAATCACCCGGATGCATGGATGCAT GGATAC (SEQ ID NO: 10) | 5' flank aplification for An ID 1117792 del cassette, Rev, flank for pyrG (pPEEL-002) |
| oPEEL-026 | GCCATGCGGGCTTGGGACGCCATGTCC GTCGCGTGATAACCAGTCGTGTTAAA GCGATCC (SEQ ID NO: 11) | 3' flank aplification for An ID 1117792 del cassette, For, flank for pyrG (pPEEL-002) |
| oPEEL-027 | AGCTCCACCGCGGTGGCGGCCGCTCTA GAACTAGTGGATCGCGGCCGCAAGGA GCGCGAGGGAATCAGC (SEQ ID NO: 12) | 3' flank aplification for An ID 1117792 del cassette, Rev, flank for EcoRI/BamHI dig pPEEL-001 |
| oPEEL-031 | CCCCCCCTCGAGGTCGACGGTATCGAT AAGCTTGATATCGGCGGCCGCGAACCA GGCGCAGCGGATC (SEQ ID NO: 13) | 5' flank aplification for An ID 1141260 del cassette, For, flank for EcoRI/BamHI dig pPEEL-001 |
| oPEEL-032 | CTGGTATAGCCAAACATCGCCAATCAC CTCAATCACCCGGCTTTCTTACGACGT TGATCC (SEQ ID NO: 14) | 5' flank aplification for An ID 1141260 del cassette, Rev, flank for pyrG (pPEEL-002) |
| oPEEL-033 | GCCATGCGGGCTTGGGACGCCATGTCC GTCGCGTGATAACGTCCTGTAGTAGTA GGATAA (SEQ ID NO: 15) | 3' flank aplification for An ID 1141260 del cassette, For, flank for pyrG (pPEEL-002) |
| oPEEL-034 | AGCTCCACCGCGGTGGCGGCCGCTCTA GAACTAGTGGATCGCGGCCGCGTTGCT ATCACAAAGGATTC (SEQ ID NO: 16) | 3' flank aplification for An ID 1141260 del cassette, Rev, flank for EcoRI/BamHI dig pPEEL-001 |
| oPEEL-036 | CCCCCCCTCGAGGTCGACGGTATCGAT AAGCTTGATATCGGCGGCCGCGTATTG GCTTAACCCACCCT (SEQ ID NO: 17) | 5' flank aplification for An ID 1121140 del cassette, For, flank for EcoRI/BamHI dig pPEEL-001 |
| oPEEL-037 | CTGGTATAGCCAAACATCGCCAATCAC CTCAATCACCCGGCGAGTGATTCTTCG ATTATA (SEQ ID NO: 18) | 5' flank aplification for An ID 1121140 del cassette, Rev, flank for pyrG (pPEEL-002) |
| oPEEL-038 | GCCATGCGGGCTTGGGACGCCATGTCC GTCGCGTGATAACCAGTAACAGTAAT CGTAGCAG (SEQ ID NO: 19) | 3' flank aplification for An ID 1121140 del cassette, For, flank for pyrG (pPEEL-002) |
| oPEEL-039 | AGCTCCACCGCGGTGGCGGCCGCTCTA GAACTAGTGGATCGCGGCCGCACGGCG CCAATGAGATATGC (SEQ ID NO: 20) | 3' flank aplification for An ID 1121140 del cassette, Rev, flank for EcoRI/BamHI dig pPEEL-001 |
| oPEEL-040 | CCCCCCCTCGAGGTCGACGGTATCGAT AAGCTTGATATCGGCGGCCGCCTAAGC TTTAGCTACAAGCA (SEQ ID NO: 21) | 5' flank aplification for An ID39114 cassette, For, flank for EcoRI/BamHI dig pPEEL-001 |
| oPEEL-041 | CTGGTATAGCCAAACATCGCCAATCAC CTCAATCACCCGGCGTTGTTACATATA GAAGCA (SEQ ID NO: 22) | 5' flank aplification for An ID39114 del cassette, Rev, flank for pyrG (pPEEL-002) |
| oPEEL-042 | GCCATGCGGGCTTGGGACGCCATGTCC GTCGCGTGATAACGTGGTCTATGTTG GATAGAT (SEQ ID NO: 23) | 3' flank aplification for An ID39114 del cassette, For, flank for pyrG (pPEEL-002) |
| oPEEL-043 | AGCTCCACCGCGGTGGCGGCCGCTCTA GAACTAGTGGATCGCGGCCGCTCCCAG TCCTCATCATCATC (SEQ ID NO: 24) | 3' flank aplification for An ID39114 del cassette, Rev, flank for EcoRI/BamHI dig pPEEL-001 |

TABLE 1-continued

Primers for the construction of gene deletion cassette, primers for colony PCR and sgRNA sequences.

| | | |
|---|---|---|
| oPEEL-044 | CCCCCCCTCGAGGTCGACGGTATCGAT<br>AAGCTTGATATCGGCGGCCGCCGACCG<br>ATGGACACTCTTGT<br>(SEQ ID NO: 25) | 5' flank aplification for An ID1170646 cassette, For, flank for EcoRI/BamHI dig pPEEL-001 |
| oPEEL-045 | CTGGTATAGCCAAACATCGCCAATCAC<br>CTCAATCACCCGGTGTAGGCAAAGGGT<br>GAGAGT<br>(SEQ ID NO: 26) | 5' flank aplification for An ID1170646 del cassette, Rev, flank for pyrG (pPEEL-002) |
| oPEEL-046 | GCCATGCGGGCTTGGGACGCCATGTCC<br>GTCGCGTGATAACCATTGGCTTCGCGC<br>TGAAAT<br>(SEQ ID NO: 27) | 3' flank aplification for An ID1170646 del cassette, For, flank for pyrG (pPEEL-002) |
| oPEEL-047 | AGCTCCACCGCGGTGGCGGCCGCTCTA<br>GAACTAGTGGATCGCGGCCGCGCAAA<br>GCAGACGTTAAGCCC<br>(SEQ ID NO: 28) | 3' flank aplification for An ID 1170646 del cassette, Rev, flank for EcoRI/BamHI dig pPEEL-001 |

Primers for colony PCR

| Name | Sequence | Description |
|---|---|---|
| oPEEL-001 | AGCTGGTATAGCCAAACATC<br>(SEQ ID NO: 29) | Rev primer for checking 5' deletion, anneals with *A. niger* pyrG used in the deletion cassettes |
| oPEEL-011 | GCTAATACGTGGTATGTATG<br>(SEQ ID NO: 30) | For primer for checking ID1146483 deletion in *A. niger*, should be used with oPEEL-001 |
| oPEEL-021 | GAAGGCAGGATTGGAGAAGG<br>(SEQ ID NO: 31) | For primer for checking ID 1090836 deletion in *A. niger*, should be used with oPEEL-001 |
| oPEEL-028 | CACGTGCTACGCCAGGTAC<br>(SEQ ID NO: 32) | For primer for checking ID 1117792 deletion in *A. niger*, should be used with oPEEL-001 |
| oPEEL-029 | GTAGCATGGAGGTAAAGTAT<br>(SEQ ID NO: 33) | For primer for checking ID 39114 deletion in *A. niger*, should be used with oPEEL-001 |
| oPEEL-030 | CAGCTATGCTACAGTATATC<br>(SEQ ID NO: 34) | For primer for checking ID1121140 deletion in *A. niger*, should be used with oPEEL-001 |
| oPEEL-035 | CAAGCTACTATCGAGCACTC<br>(SEQ ID NO: 35) | For primer for checking ID1141260 deletion in *A. niger*, should be used with oPEEL-001 |
| oPEEL-048 | GTAGACTACCAAGTCGTAGT<br>(SEQ ID NO: 36) | For primer for checking ID 1170646 deletion in *A. niger*, should be used with oPEEL-001 |
| oPEEL-059 | TTGAGCTCGTGTGTCTGGAC<br>(SEQ ID NO: 37) | For checking mixed population. Amplify ORF ID 39114, FOR |
| oPEEL-060 | ACAGCGGCTAGATAACGAGC<br>(SEQ ID NO: 38) | For checking mixed population. Amplify ORF ID 39114, REV |
| oPEEL-061 | GATACATGGGCAGCGATGGA<br>(SEQ ID NO: 39) | For checking mixed population. Amplify ORF ID 1090836, FOR |
| oPEEL-062 | CTCTCCTCACCCACCTCTGA<br>(SEQ ID NO: 40) | For checking mixed population. Amplify ORF ID 1090836, REV |
| oPEEL-063 | ATGACCATCACCGAACCCAC<br>(SEQ ID NO: 41) | For checking mixed population. Amplify ORF ID 1117792, FOR |
| oPEEL-064 | GGCTCGCGCAAACTGAATAG<br>(SEQ ID NO: 42) | For checking mixed population. Amplify ORF ID 1117792, REV |

TABLE 1-continued

Primers for the construction of gene deletion cassette, primers for colony PCR and sgRNA sequences.

| | | |
|---|---|---|
| oPEEL-065 | CAAGGTCATCGTCGCGGATA (SEQ ID NO: 43) | For checking mixed population. Amplify ORF ID 1141260, FOR |
| oPEEL-066 | CCAACGGCACATTTCCGATG (SEQ ID NO: 44) | For checking mixed population. Amplify ORF ID 1141260, REV |
| oPEEL-067 | GCATAGCAGTGCTTCTTCGC (SEQ ID NO: 45) | For checking mixed population. Amplify ORF ID 1121140, FOR |
| oPEEL-068 | CTCCGTTGTTCACTCCGTCA (SEQ ID NO: 46) | For checking mixed population. Amplify ORF ID 1121140, REV |
| oPEEL-071 | GCTGGCTTTTCGTCAAGGTG (SEQ ID NO: 47) | For checking mixed population. Amplify ORF ID 1146483, FOR |
| oPEEL-072 | GCTTGATAGCTTCGGGGTGT (SEQ ID NO: 48) | For checking mixed population. Amplify ORF ID 1146483, REV |
| oPEEL-073 | GCCCATAATCCTCCACCTCG (SEQ ID NO: 49) | For checking mixed population. Amplify ORF ID 1170646, FOR |
| oPEEL-074 | CAGTCAACGGACAATGCACC (SEQ ID NO: 50) | For checking mixed population. Amplify ORF ID 1170646, REV |
| oPEEL-088 | CCCCTATACCCGTCTGTTTG (SEQ ID NO: 51) | For primer for checking 3' deletion, anneals with *A. niger* pyrG used in the deletion cassettes |
| oPEEL-089 | CCATGGCATCCTCGAGCTCC (SEQ ID NO: 52) | Rev primer for checking deletion ID 39114 in *A. niger*, used with oPEEL-088, ~1.7 kb |
| oPEEL-090 | GTTGTTCATCGATTCCCCCG (SEQ ID NO: 53) | Rev primer for checking deletion ID 1090836 in *A. niger*, used with oPEEL-088, ~1.7 kb |
| oPEEL-091 | CATCCTCGACTGCAGCAATG (SEQ ID NO: 54) | Rev primer for checking deletion ID 1117792 in *A. niger*, used with oPEEL-088, ~1.7 kb |
| oPEEL-092 | CGTACTGTCAGAGCAACCGA (SEQ ID NO: 55) | Rev primer for checking deletion ID 1141260 in *A. niger*, used with oPEEL-088, ~1.7 kb |
| oPEEL-093 | CCGGGGGTAATAGTAGTCGC (SEQ ID NO: 56) | Rev primer for checking deletion ID 1121140 in *A. niger*, used with oPEEL-088, ~1.7 kb |
| oPEEL-095 | GTGCTCTTCTAGGTTCCGAG (SEQ ID NO: 57) | Rev primer for checking deletion ID 1146483 in *A. niger*, used with oPEEL-088, ~1.7 kb |
| oPEEL-096 | GGCGGCACCGTCCGTGTGTG (SEQ ID NO: 58) | Rev primer for checking deletion ID 1170646 in *A. niger*, used with oPEEL-088, ~1.7 kb | sgRNA sequences

| Protospacer sequence (20 bp) | Target |
|---|---|
| TATCACCTCCGCATAACCAT (SEQ ID NO: 59) | 5' 1090836 |
| AGTTCAGTCTCTGTGGAGGA (SEQ ID NO: 60) | 3' 1090836 |
| ATGCATCCATTTTAGAGCCA (SEQ ID NO: 61) | 5' 1117792 |
| TCTGGAAGTCGCTGTGCCCT (SEQ ID NO: 62) | 3' 1117792 |
| TATCGCCAGAACAAAAAGCG (SEQ ID NO: 63) | 5' 1141260 |

TABLE 1-continued

Primers for the construction of gene deletion cassette, primers for colony PCR and sgRNA sequences.

| | | |
|---|---|---|
| AGACCGATCATTATTGACGA (SEQ ID NO: 64) | 3' | 1141260 |
| TCGTGTCTGACATTCCACAA (SEQ ID NO: 65) | 5' | 1121140 |
| ACAGAGTTCTATTCACGGGT (SEQ ID NO: 66) | 3' | 1121140 |
| TGTTACCCCCACGCGGGGTA (SEQ ID NO: 67) | 5' | 1146483 |
| AGACTTGTAGGCCAGGATGT (SEQ ID NO: 68) | 3' | 1146483 |
| AGGCAAAGGGTGAGAGTAGT (SEQ ID NO: 69) | 5' | 1170646 |
| AGCTCCCCCTGCCTCCTCG (SEQ ID NO: 70) | 3' | 1170646 |
| TCCACGATGCCCTACACACC (SEQ ID NO: 71) | | 39114 |

1.5. Chemical Analyses

Samples were removed from liquid cultivations at intervals and mycelium was separated from the supernatant by filtration. The concentration of mesogalactaric acid and D-galacturonic acid was determined by HPLC using a Fast Acid Analysis Column (100 mm×7.8 mm, BioRad Laboratories, Hercules, Calif.) linked to an Aminex HPX-87H organic acid analysis column (300 mm×7.8 mm, BioRad Laboratories) with 5.0 mM $H_2SO_4$ as eluent and a flow rate of 0.5 ml $min^{-1}$. The column was maintained at 55° C. Peaks were detected using a Waters 2489 UV/Visible dual wavelength UV (210 nm) detector.

2. RESULTS 2.1. RNA Sequencing

A. niger wild type mycelium was cultivated on meso-galactaric acid and the utilization of meso-galactaric acid was monitored using HPLC (data not shown). It was indeed confirmed that A. niger is capable of catabolizing meso-galactaric acid. In addition, we observed that oxalic acid was produced in the cultivation. For the RNA sequencing, total RNA was extracted after 0, 5 and 18 hours and sequenced. The results from the RNA sequencing are presented in FIG. 2.

2.2. CRISPR/Cas9 Mediated Gene Deletions

Figure 2:
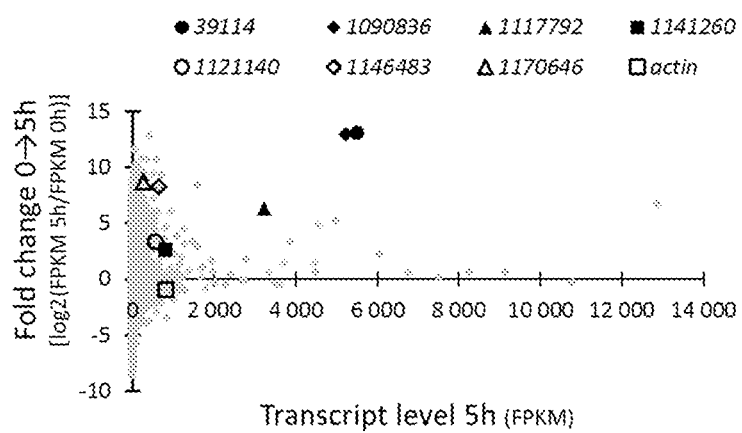
FIG. 2 shows results of RNA sequencing of *A. niger* at 0 hours and 5 hours after the shift to meso-galactaric acid. Fold change in transcript levels between 0 and 5 hours on y-axis and transcript levels after 5 hours on x-axis.

We selected seven putative genes based on their induction on meso-galactaric acid and relevant enzyme prediction for carbohydrate metabolism (FIG. 2 and Table 2). These genes were deleted from the uracil auxotrophic strain A. niger ΔpyrG. We used deletion cassettes containing homologous flanking regions (1.5 kb) for the target gene and pyrG as selectable marker. One of the genes (ID 39114) was deleted by using only the deletion cassette and uracil-deficient medium for selection. For rest of the genes, we used CRISPR/Cas9 technology implemented through the AMA plasmid pFC-332 (Nodvig et al., 2015) expressing Cas9 together with the selectable marker hyg for hygromycin. Instead of expressing the sgRNA from the plasmid, we used two in vitro synthetized sgRNAs for each gene which were delivered together with the Cas9 plasmid and deletion cassette in the transformation. Uracil-deficient medium supplemented with hygromycin was used in the gene deletions utilizing the CRISPER/Cas9 technology generating selection pressure for the cassette and for the Cas9 plasmid. For six of the target genes both deletion methods were used. The frequency of correct gene deletions improved dramatically when Cas9 and in vitro synthesized sgRNAs were used (Table 3).

TABLE 2

Genes selected for deletion based on RNA sequencing of A. niger wild type strain cultivated on meso-galactaric acid. Transcript levels are presented as fragments per kilobase of exon per million fragments mapped (FPKM). Protein ID is based on Joint Genome institute (JGI).

| Protein | Meso-galactaric acid | | | |
|---|---|---|---|---|
| ID | 0 h | 5 h | 18 h | InterPro/KOG prediction |
| 39114 | 1 | 5497 | 4219 | AMP-dependent synthetase and ligase, α-aminoadipate-semialdehyde dehydrogenase |
| 1090836 | 1 | 5239 | 6627 | Aldo/keto reductase |
| 1117792 | 42 | 3239 | 1050 | Alcohol dehydrogenase, zinc-binding |
| 1141260 | 132 | 805 | 747 | Short-chain dehydrogenase/reductase |
| 1121140 | 51 | 545 | 1162 | FAD-dependent oxidoreductase |
| 1146483 | 2 | 641 | 1661 | Mandelate racemase/muconate lactonizing enzyme |
| 1170646 | 1 | 260 | 164 | D-isomer specific 2-hydroxyacid dehydrogenase |

TABLE 3

Frequency of the correct gene deletion with and without CRISPR/Cas9.

| | Protein ID | Screened | Correct | Frequency (%) |
|---|---|---|---|---|
| no CRISPR/Cas9 | 39114 | 30 | 2 | 6.7 |
| CRISPR/Cas9 | 1090836 | 30 | 1 | 3.3 |
| | 1117792 | 30 | 13 | 43.3 |
| | 1141260 | 30 | 0 | 0.0 |
| | 1121140 | 60 | 1 | 1.7 |
| CRISPR/Cas9 + in vitro sgRNA | 1090836 | 40 | 11 | 27.5 |
| | 1117792 | 8 | 8 | 100 |
| | 1141260 | 8 | 8 | 100 |
| | 1121140 | 8 | 3 | 37.5 |
| | 1146483 | 8 | 7 | 87.5 |
| | 1170646 | 8 | 5 | 62.5 |

The non-homologous end joining (NHEJ) pathway is the predominant mechanism for DNA repair in *A. niger*. Thus the frequency of homologous recombination is typically low in transformations. Previously, CRISPR/Cas9 mediated gene deletions were described in several *Aspergillus* species by using the AMA plasmid expressing both Cas9 protein and sgRNA (Nodvig et al., 2015). Due to the poor availability of characterized RNA polymerase (RNA pol) III promoters, sgRNA was expressed under a RNA pol II promoter which requires the use of additional ribozyme structures to release a functional sgRNA. In *A. niger*, transformation of the plasmid without donor DNA resulted in successful gene disruptions via short deletions by the NHEJ mediated repair. In the present study, we used in vitro synthesized sgRNAs. This approach has been described earlier in the filamentous fungi *Trichoderma reesei* (Liu et al., 2015), *Penicillium chrysogenum* (Pohl et al., 2016) and *Aspergillus fumigatus* (C. Zhang et al., 2016) but not in *Aspergillus niger*. We also decided to use deletion cassettes as donor DNA. This approach allowed double selection resulting in high frequencies of correct deletions. The use of donor DNA allows easier screening of the genotypes by colony PCR which would not necessary detect short deletions in the genome resulting from NHEJ pathway repair without donor DNA.

2.3. Disruption of Meso-Galactaric Acid Catabolism

The resulting mutant strains from the gene deletions were tested for meso-galactaric acid consumption in liquid cultivations (FIG. 3). We observed that the consumption of meso-galactaric acid on minimal medium without any other carbon source was very poor even by the wild type strain (data not shown). Thus, we tested all the mutant strains on minimal medium containing meso-galactaric acid and D-xylose (FIG. 3A) and on YP-medium containing meso-galactaric acid (FIG. 3B). Both conditions resulted in similar observation—strains Δ39114, Δ1090836 and Δ1121140 had disrupted or reduced catabolism of meso-galactaric acid. In the case of Δ39114, the catabolism was completely blocked in both conditions while Δ1090836 and Δ1121140 showed minor and moderate meso-galactaric acid consumption on YP-medium, respectively.

The protein 39114 has a predicted function of α-aminoadipate-semialdehyde dehydrogenase (EC 1.2.1.31) also known as α-aminoadipate reductase (AAR) (Napora-Wijata et al., 2014). The proteins 1090836 and 1121140 have predicted functions of aldo/keto reductase and FAD-dependent oxidoreductase, respectively. Enzymatic activities of these proteins also remain unknown.

2.4. Engineering *A. niger* for Meso-Galactaric Acid Production

The genes with the ID 39114, 1090836 and 1121140 were deleted from the *A. niger* strain ΔgaaA-udh. The strain ΔgaaA-udh has a disrupted pathway for D-galacturonic acid catabolism (deletion of gaaA); however, introduction of udh regenerated the catabolism of D-galacturonic acid with only minor production of meso-galactaric acid (Mojzita et al., 2010). The strain was uracil autotroph (+pyrG) and we decided to use the same deletion cassettes containing pyrG selectable marker which were used in the initial gene deletions from ΔpyrG strain. This time we combined the deletion cassette with the Cas9 plasmid and in vitro synthesized sgRNA. Consequently, the selection pressure was only for the Cas9 plasmid but not for the donor DNA. Nevertheless, about 1 out of 10 screened colonies revealed the correct gene deletion.

Next the resulting strain ΔgaaA-Δ39114-udh was tested for meso-galactaric acid production in shake flask cultivations on D-galacturonic acid (FIG. 4). Meso-galactaric acid concentrations of around 1.5 $gl^{-1}$ were observed in the minimal medium without (FIG. 4A) and with (FIG. 4B) co-substrate by ΔgaaA-Δ39114-udh strain while ΔgaaA-udh did not accumulate meso-galactaric acid. On rich YP-medium, the production increased and reached values above 4 $gl^{-1}$ by the ΔgaaA-Δ39114-udh (FIG. 4C). The strain ΔgaaA-udh started to produced meso-galactaric acid after 96 hours; however, values remained about four-fold lower when compared to ΔgaaA-Δ39114-udh strain. In terms of product yields, ΔgaaA-Δ39114-udh was superior—approximately all the consumed D-galacturonic acid was converted to meso-galactaric acid. Similar yields were observed with the strains ΔgaaA-Δ1090836-udh and ΔgaaA-Δ1121140-udh. With ΔgaaA-udh strain, only about 7% of consumed D-galacturonic acid was converted to meso-galactaric acid.

Figure 5:
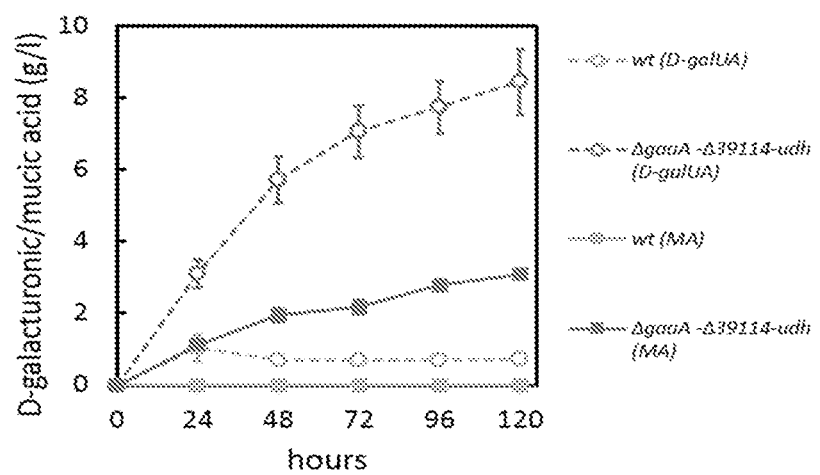
FIG. 5 shows results of the consolidated bioprocess from orange processing waste by the wild type strain (grey symbols) and ΔgaaA-Δ39114-udh (black symbols). Concentrations of D-galacturonic acid (D-galUA, open circles) and meso-galactaric acid (MA, squares) are presented. Data represent means ± standard deviation from three replicates. If error bars are not visible they are smaller than the symbol.

We also wanted to investigate the consolidated bioprocess for the production directly from pectin-rich biomass. Processing waste from orange juice industry was used as substrate in submerged cultivations (FIG. 5). As a result, 3.1 $gl^{-1}$ meso-galactaric acid was produced from 37.4 $gl^{-1}$ (dry mass) orange processing waste by the ΔgaaA-Δ39114-udh. The content of D-galacturonic acid in the waste is about 27% (Kuivanen et al., 2014) resulting in a maximum theoretical meso-galactaric acid concentration of around 10 $gl^{-1}$ that can be achieved. In addition to meso-galactaric acid, 8.4 $gl^{-1}$ free D-galacturonic acid was observed in the cultivations after 120 h. The sum of observed meso-galactaric and D-galacturonic acid corresponds approximately to the total D-galacturonic acid content in the orange processing waste. In contrast, the wild type strain likely consumed most of the D-galacturonic acid released from the substrate and only low concentrations were observed during the cultivations. To sum up, the process for consolidated meso-galactaric acid production resulted in the product titer of about 30% of theoretical maximum by the ΔgaaA-Δ39114-udh. Similar results were observed with the strains ΔgaaA-Δ1090836-udh and ΔgaaA-Δ1121140-udh. We did not optimize the process and thus, with careful process optimization, the remaining D-galacturonic acid may be converted to meso-galactaric acid by the engineered strain.

REFERENCES

Barratt, R., Johnson, G., Ogata, W., 1965. Wild-type and mutant stocks of *Aspergillus nidulans*. Genetics 52, 233-246.

Benz, J. P., Protzko, R. J., Andrich, J. M., Bauer, S., Dueber, J. E., Somerville, C. R., 2014. Identification and characterization of a galacturonic acid transporter from Neurospora crassa and its application for *Saccharomyces cerevisiae* fermentation processes. Biotechnol. Biofuels 7, 20. doi:10.1186/1754-6834-7-20.

Chang Y F, Feingold D S (1969) Hexuronic acid dehydrogenase of *Agrobacterium tumefaciens*. J Bacterid. 99:667-673.

Chang, Y. F., Feingold, D. S., 1970. D-Glucaric acid and galactaric acid catabolism by *Agrobacterium tumefaciens*. J. Bacteriol. 102, 85-96.

Coen D. M. 2001. The poymerase chain reaction, published in Ausubel F M, Brent R, Kingston R E, More D D, Seidman J G, Smith K. and Struhl K (eds.) Cur-rent protocols in molecular biology. John Wiley & Sons. Inc., Hoboken, USA.

Dagley, S., Trudgill, P. W., 1965. The metabolism of galactarate, D-glucarate and various pentoses by species of *Pseudomonas*. Biochem. J. 95, 48-58.

Gellissen G (ed). 2005. Production of recombinant proteins. Novel microbial and eucaryotic expression systems. Wiley-VCH Verlag GmbH & Co, Weinheim, Germany.

Kuivanen, J., Dantas, H., Mojzita, D., Mallmann, E., Biz, A., Krieger, N., Mitchell, D., Richard, P., 2014. Conversion of orange peel to L-galactonic acid in a consolidated process using engineered strains of *Aspergillus niger*. AMB Express 4, 33. doi:10.1186/s13568-014-0033-z Kuivanen, J., Penttilä, M., Richard, P., 2015. Metabolic engineering of the fungal D-galacturonate pathway for L-ascorbic acid production. Microb. Cell Fact. 14, 1-9. doi:10.1186/s12934-014-0184-2

Kuivanen et al. 2016. A novel pathway for fungal D-glucuronate catabolism contains an L-idonate forming 2-keto-L-gulonate reductase. Scientific Reports 6:26329.

Liu, R., Chen, L., Jiang, Y., Zhou, Z., Zou, G., 2015. Efficient genome editing in filamentous fungus *Trichoderma reesei* using the CRISPR/Cas9 system. Cell Discov. 1, 15007. doi:10.1038/celldisc.2015.7

Mohnen, D. 2008, "Pectin structure and biosynthesis", Current opinion in plant biology, vol. 11, no. 3, pp. 266-277.

Mojzita, D., Wiebe, M., Hilditch, S., Boer, H., Penttila, M., Richard, P., 2010. Metabolic engineering of fungal strains for conversion of D-galacturonate to mesogalactarate. Appl. Environ. Microbiol. 76, 169-175. doi:10.1128/AEM.02273-09

O'Neill, M. A., Ishii, T., Albersheim, P. & Darvill, A. G. 2004, Rhamnogalacturonan II: Structure and function of a borate cross-linked cell wall pectic polysaccharide.

Napora-Wijata, K., Strohmeier, G. A., Winkler, M., 2014. Biocatalytic reduction of carboxylic acids. Biotechnol. J. 9, 822-843. doi:10.1002/biot.201400012

Nodvig, C. S., Nielsen, J. B., Kogle, M. E., Mortensen, U. H., 2015. A CRISPR-Cas9 system for genetic engineering of filamentous fungi. PLoS One 10, 1-18. doi:10.1371/journal.pone.0133085

Pohl, C., Kiel, J. A. K., Driessen, A. J. M., Bovenberg, R. A. L., Nygård, Y., 2016. CRISPR/Cas9 based genome editing of *Penicillium chrysogenum*. ACS Synth. Biol. acssynbio.6b00082. doi:10.1021/acssynbio.6b00082

Richard, P., & Hilditch, S. (2009). D-galacturonic acid catabolism in microorganisms and its biotechnological relevance. Applied Microbiology and Biotechnology, 82(4), 597-604. doi:10.1007/s00253-009-1870-6.

Richard et al. J Biol Chem. 276: 40631-40637.

Rautiainen, S., Lehtinen, P., Chen, J., Vehkamäki, M., Niemelä, K., Leskelä, M., Repo, T., 2015. Selective oxidation of uronic acids into aldaric acids over gold catalyst. RSC Adv. 5, 19502-19507. doi:10.1039/C5RA01802A Zhang, C., Meng, X., Wei, X., Lu, L., 2016. Highly efficient CRISPR mutagenesis by microhomology-mediated end joining in *Aspergillus fumigatus*. Fungal Genet. Biol. 86, 47-57. doi:10.1016/j.fgb.2015.12.007

Zhang, H., Li, X., Su, X., Ang, L., Zhang, Y., 2016. Production of Adipic Acid from Sugar Beet Residue by Combined Biological and Chemical Catalysis 1-8. doi: 10.1002/cctc.201600069

The invention claimed is:

1. A method for producing meso-galactaric acid, said method comprising
contacting a fungal cell genetically modified to express uronate dehydrogenase enzyme, genetically modified to have reduced D-galacturonic acid reductase activity, and modified to reduce meso-galactaric acid catabolism by deleting at least part of a gene encoding JGI protein IDs: 39114 (SEQ ID No: 72), 1090836 (SEQ ID NO: 73) and/or 1121140 (SEQ ID NO: 74), with a biomaterial comprising galacturonic acid, and
recovering the resulting meso-galactaric acid.

2. A fungal cell that has been genetically modified to express uronate dehydrogenase enzyme, genetically modified to have reduced D-galacturonic acid reductase activity, and is capable of converting D-galacturonic acid to meso-galactaric acid, wherein said fungal cell has been further modified to reduce meso-galactaric acid catabolism by deleting at least part of a gene encoding JGI protein IDs: 39114 (SEQ ID No: 72), 1090836 (SEQ ID NO: 73) and/or 1121140 (SEQ ID NO: 74).

3. A method for treating biomaterial comprising galacturonic acid, which method comprises that a fungal cell genetically modified to express uronate dehydrogenase enzyme, genetically modified to have reduced D-galacturonic acid reductase activity, and modified to reduce mesogalactaric acid catabolism by deleting at least part of a gene encoding JGI protein IDs: 39114 (SEQ ID No: 72), 1090836 (SEQ ID NO: 73) and/or 1121140 (SEQ ID NO: 74), is contacted with said biomaterial under suitable culture conditions.

4. The method of claim 1, wherein the fungal cell is a mould or filamentous fungus.

5. The method of claim 1, wherein the fungal cell is from the genera *Aspergillus*, *Hypocrea* or *Trichoderma*.

6. The method of claim 1, wherein the fungal cell is selected from the group consisting of *Aspergillus niger, A. oryzae, A. terreus, A. nidulans, A. kawachii, A. fischeri* and *Trichoderma reesei*.

7. The method of claim 1, wherein the fungal cell is naturally capable of degrading pectin.

8. The method of claim 1, wherein the uronate dehydrogenase enzyme is a heterologous uronate dehydrogenase enzyme.

9. The method of claim 1, wherein the uronate dehydrogenase enzyme is D-galacturonate dehydrogenase enzyme.

10. The method of claim 1, wherein a polynucleotide encoding D-galacturonic acid reductase has been deleted.

11. The method of claim 1, wherein the fungal cell has further been genetically modified by deleting at least part of a polynucleotide encoding 2-keto-3-deoxy-L-galactonate aldolase.

12. The method of claim 1, wherein the uronate dehydrogenase enzyme is a heterologous uronate dehydrogenase enzyme originating from *Pseudomonas* or *Agrobacterium* genera.

* * * * *